United States Patent [19]
Witt et al.

[11] Patent Number: 5,795,860
[45] Date of Patent: Aug. 18, 1998

[54] ANALOGS FOR SPECIFIC OLIGOSACCHARIDE-PROTEIN INTERACTIONS AND USES THEREFOR

[75] Inventors: Daniel P. Witt, Hamilton; Walter C. Herlihy, Jr., Beverly, both of Mass.

[73] Assignee: Repligen Corporation, Needham, Mass.

[21] Appl. No.: 202,989

[22] Filed: Feb. 28, 1994

Related U.S. Application Data

[63] Continuation-in-part of Ser. No. 24,558, Mar. 1, 1993, abandoned.

[51] Int. Cl.$^6$ .......................... A01N 37/18; A61K 31/70
[52] U.S. Cl. .......................... 514/12; 514/2; 514/54; 514/62; 530/350; 530/359; 536/55.1; 536/55.2
[58] Field of Search .................. 514/54, 56, 2, 514/12, 62; 536/55.1; 530/55.2, 350, 359

[56] References Cited

U.S. PATENT DOCUMENTS

| | | | |
|---|---|---|---|
| 4,826,827 | 5/1989 | Lormeau et al. | 514/56 |
| 5,079,228 | 1/1992 | Cohen et al. | 514/12 |
| 5,084,564 | 1/1992 | Vila et al. | 536/21 |
| 5,112,946 | 5/1992 | Maione | 530/324 |
| 5,116,483 | 5/1992 | Lander | 204/299 |
| 5,158,940 | 10/1992 | Larocca et al. | 514/54 |
| 5,164,295 | 11/1992 | Kisilevsky et al. | 435/7.8 |
| 5,262,403 | 11/1993 | Nicholson et al. | 514/56 |
| 5,380,716 | 1/1995 | Conrad et al. | 514/56 |

FOREIGN PATENT DOCUMENTS

| | | | |
|---|---|---|---|
| 454 220 A1 | 10/1991 | European Pat. Off. | |
| 0 361 960A2 | 4/1992 | European Pat. Off. | G01R 33/48 |
| 0 509 517 | 4/1992 | European Pat. Off. | |
| 0 506 325A1 | 9/1992 | European Pat. Off. | A61K 31/725 |
| 0 509 120A1 | 10/1992 | European Pat. Off. | A61K 31/725 |
| 0 511 830A2 | 11/1992 | European Pat. Off. | C08B 37/10 |
| 529 715 A1 | 3/1993 | European Pat. Off. | |
| WO 90/06755 | 6/1990 | WIPO | A61K 31/70 |
| WO90/15816 | 12/1990 | WIPO | |
| WO91/13624 | 9/1991 | WIPO | |
| WO 91/19502 | 12/1991 | WIPO | A61K 31/70 |
| WO93/07864 | 4/1993 | WIPO | |
| WO93/09800 | 5/1993 | WIPO | |
| WO93/20202 | 10/1993 | WIPO | |

OTHER PUBLICATIONS

Lee et al., Proc. Natl. Acad. Sci. USA 88:2768–277 (1991) Analysis of Affinity & structural selectivity . . . electrophoretic approach.
Rot, Cytokine, 4(5) 347–352 (1992) "Binding of Neutrophil Attractant/Activation . . . Derman Cells".
Tanaka et al., Nature 361:79–82 (1993) "T–Cell Adhesion Induced by proteoglycan–immobilized . . . MIP–1B".
Turnbull et al., Journal of Bio. Chem. 267(15):10337–10341 (1992) "Identification of the Basic Fibroblast . . . Sulfate".
Habuchi et al. Biochem. J. 285:805–813 (1992) "Structure of a Heparan Sulphate Oligosaccharide . . . Fibroblast Growth Factor".
Plate et al., Nature 359:845–848 (1992) "Vascular Endothelial Growth Factor is a Potential Tumor . . . Gliomas In Vivo".
Shweiki et al., Nature 359:843–845 (1992) "Vascular Endothelial Induced by Hypoxia . . . Angiogenesis".
Tischer et al., Journal of Bio. Chem. 266(18) 11947–11954 (1991) "The Human Gene for Vascular . . . Growth Factor".
Gallagher et al., Glycobiology 2(6)523–528 (1992) "Heparan Sulphate in the Binding . . . Growth Factor".
Rapraeger et al. Reports (1991) 1705–1708 "Requirement of Heparan Sulfate . . . Differentiation".
Yayon et al. Cell 64:841–848 (1991) "Cell Surface, Haparin–Like Molecules . . . Receptor".
Oppenheim et al., Annu. Rev. Immunol. 9:617–647 (1991) "Properties of the Novel Proinflammatory Supergene . . . Cytokine Family".
Butcher, Cell 67:1033–1036 (1991) "Leukocyte–Endothelial Cell Recognition: Three (or More) . . . Diversity".
Kjellen et al. Annu. Rev. Biochem 60:443–475 (1991) "Proteoglycans: Structures and Interactions".
Jackson et al., Physio. Review 71(2):481–539 (1991) "Glycosaminoglycans: Molecular Properties, Protein . . . Processes".
Tanaka et al., Immunology Today, 14(3):111–115 (1993) "Proteoglycans on Endothelial Cells Present Adhesion–Inducing . . . Leukocytes".
Kan et al., Science 259:1918–1921 (1993) "An Essential Heparin–Binding Domain in the Fibroblast Growth Factor Receptor Kinase".
Wing et al., "Use of large–scale hydrazinolysis in the preparation of N–of N–linked oligosaccharide libraries: application to brain issue", Glycoconjugate Journal, 9:293–301 (1992).
Mizuochi et al., "A Library of Oligosaccharide Probes (Neoglycolipids) from N–Glycosylated Proteins Reveals That Conglutinin Binds to Certain Complex–type as Well as High Mannose–type Oligosaccharide Chains", The Journal of Biological Chemistry, 264:13834–13839 (1989).
Segarini et al., "The High Molecular Weight Receptor to Transforming Growth Factor–β Contains Glycosaminolgycan Chains," J. Biol. Chem., vol. 263, No. 17, pp. 8366–8370, 1988.
Cheifetz et al., "Transforming Growth Factor–β (TGF–β) Receptor Proteoglycan," J. Biol. Chem., vol. 2664, No. 20, pp. 12025–12028, 1989.
Andres et al., "Binding of Two Growth Factor Families to Separate Domains of the Proteoglycan Betaglycan," vol. 267, No. 9, pp. 5927–5930, 1992.
Cheifetz et al., "The Transforming Growth Factor–β Receptor Type III is a Membrane Proteoglycan," J. Biol. Chem., vol. 263, No. 32, pp. 16984–16991, 1988.

*Primary Examiner*—Elli Peselev
*Attorney, Agent, or Firm*—Testa, Hurwitz & Thibeault, LLP

[57] ABSTRACT

Disclosed are (1) methods for identifying natural and synthetic sequences having binding specificity for glycan-binding proteins, including proteins that act as effectors of biological activity, (2) compositions and methods of producing protein-specific glycosaminoglycan sequence and ligand antagonists capable of modulating the effector function of these ligands, and therapeutic compositions comprising these antagonists; and 3) compositions and methods for producing protein-specific glycosaminoglycan sequence analogs useful as agonists, and therapeutic compositions comprising these agonists.

67 Claims, 16 Drawing Sheets

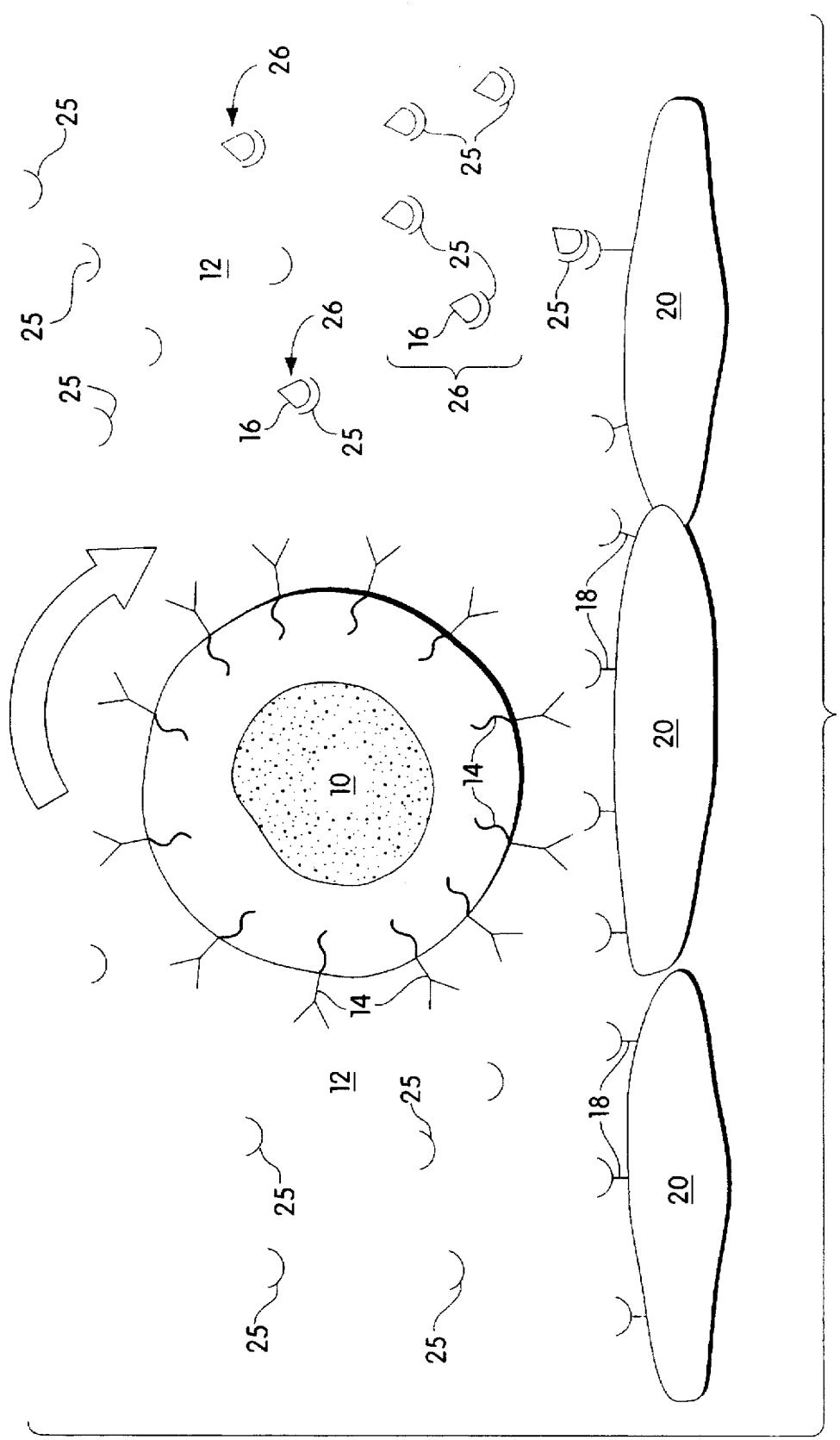

PF4    CLDLQAPLYKKIIKKLLES 70
IL8    CLDPKENWVQRVVEKFLKRAENS 72
NAP-2  CLDPDAPRIKKIVQKKLAGDESAD 71
GROα   CLNPASPIVKKIIEKMLNSDKSNY 74
                    ↑

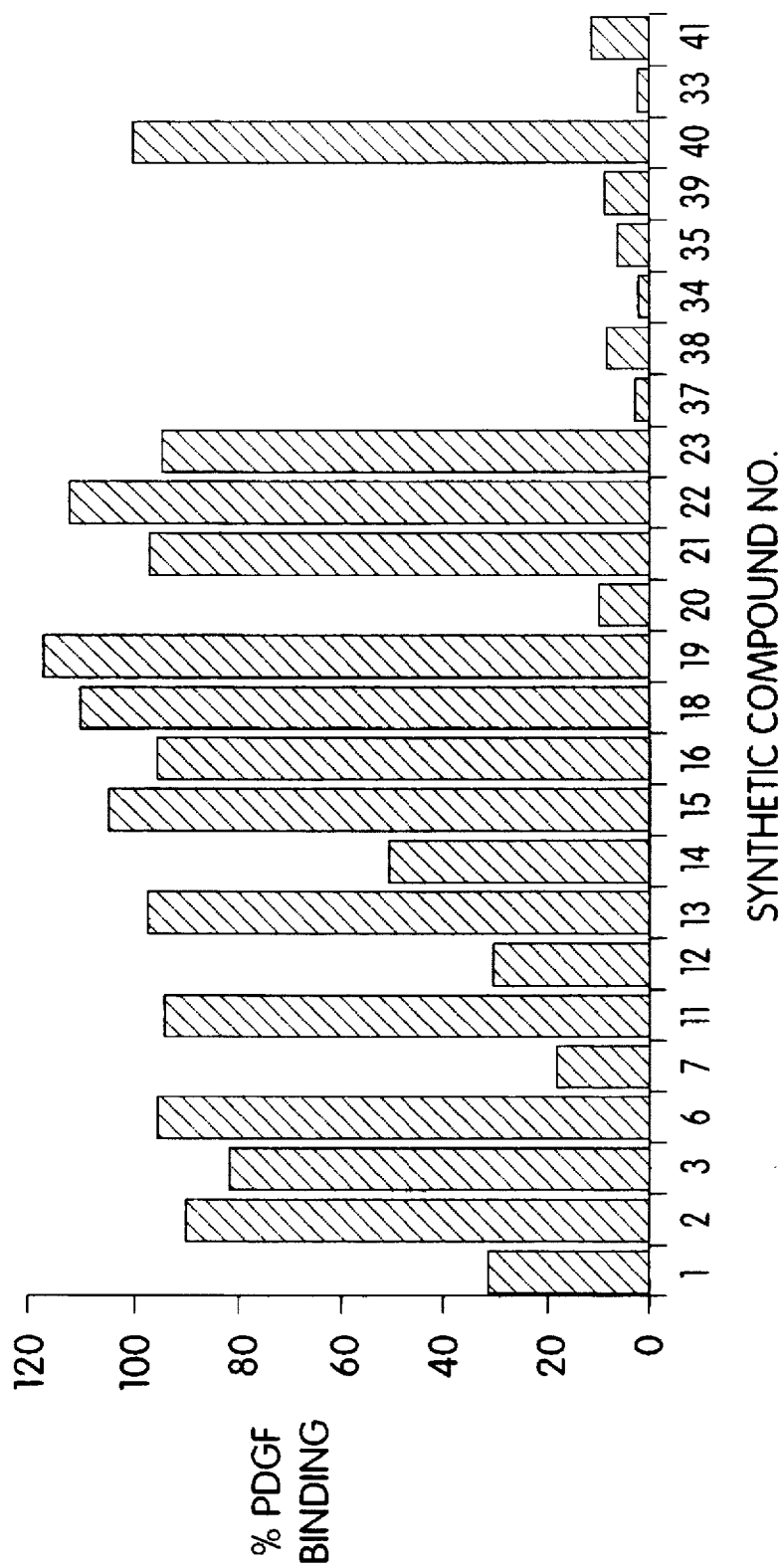

ANALOGS FOR SPECIFIC OLIGOSACCHARIDE-PROTEIN INTERACTIONS AND USES THEREFOR

CROSS-REFERENCE TO RELATED APPLICATIONS

This application is continuation-in-part of U.S. patent application Ser. No. 08/024,558, filed Mar. 1, 1993, now abandoned, the disclosure of which is incorporated herein by reference.

FIELD OF THE INVENTION

The present application relates to the field of protein-glycosaminoglycan interactions and, more particularly, to means and compositions for mimicking the specificity of this interaction.

BACKGROUND OF THE INVENTION

Glycosaminoglycan Structure

Glycosaminoglycans (GAG) are naturally-occurring carbohydrate-based molecules implicated in regulation of a number of cellular processes, including blood coagulation, angiogenesis, tumor growth, nerve cell development, smooth muscle cell proliferation, and gene expression, most likely by interaction with effector molecules. GAG's are linear, non-branched chains of repeating two-sugar (disaccharide) units which may be up to 150 units in length, and are well known and described in the art. See, for example, Jackson et al. (1991) *Physiological Reviews* 71:481-539 and Kjellen et al. (1991) *Ann. Rev. Biochem.* 60:443-475. GAG's are often, but not always, found covalently bound to protein cores in structures called proteoglycans. Proteoglycan structures are abundant on cell surfaces and are associated with the extracellular matrix around cells.

Glycosaminoglycans (also referred to herein and in the art as "glycans") can be divided into four main classes on the basis of the repeating disaccharide unit in the backbone. Typically, one sugar is a uronic acid, and the other is either an N-acetylglucosamine or an N-acetylgalactosamine. The classes are exemplified by the following four GAGs: (1) heparan sulfate (D-glucuronic acid/N-acetyl- or N-sulfo-D-glucosamine); (2) chondroitin/dermatan sulfate (D-glucuronic acid or L-iduronic acid/N-acetyl-D-glactosamine); (3) keratan sulfate (D-galactose/N-acetyl-D-glucosamine), and (4) hyaluronic acid. All GAG's, with the exception of hyaluronic acid, contain sulfate groups variously esterified to the ring hydroxyl groups of the sugars. These negatively charged groups are believed to figure prominently in the biological properties attributed to glycosaminoglycans. The naturally-occurring forms of GAG's, particularly heparin, heparan sulfate, chondroitin sulfate and dermatan sulfate, in fact are complex hetero-oligosaccharides composed of mixtures of differentially sulfated sugar residues.

One of the most thoroughly studied glycosaminoglycans is the widely used anticoagulant heparin. Heparin is a highly sulfated form of heparan sulfate, which is found in most cells. As a commercial product, heparin is a hetero-oligodisaccharide composition of about 20–60 monomeric units, having an overall extended length of about 100–300 Å, having no protein associated with it, and its anticoagulant properties can be ascribed exclusively to the specific sulfation patterns found on the carbohydrate chains. So-called "low molecular weight" heparin typically is a hetero-oligodisaccharide composition of about 25–30 monomeric units, having an overall extended length of about 40 Å. Heparin is known to have a variety of potentially useful biological activities beyond its ability to inhibit blood coagulation including, for example, the ability to block complement activation, smooth muscle cell proliferation and tumor growth. However, the toxicity of heparin at the levels required to manifest these activities in vivo has limited its clinical use. Heparan sulfate, the predominant GAG on cell surfaces, contains fewer sulfate groups than heparin and has been shown to contain regions of high sulfation interspersed among regions of low or no sulfation.

Other polysulfonated compounds described in the art and asserted to have clinically useful activities analogous to those attributed to heparin include fractions or fragments of the naturally-occurring GAG's, pentosan polysulfate (PPS), dextran sulfate, chondroitin sulfate, and keratan sulfate; and suramin, a polysulfonated napthylurea whose structural motif likely mimics that of a GAG sequence. As for heparin, the toxicity of these compounds at the levels required for therapeutic utility has limited their clinical use. A representative listing of publications describing these compounds and their asserted biological activities includes: U.S. Pat. No. 5,158,940 issued Oct. 27, 1992; U.S. Pat. No. 4,826,827, issued May 2, 1989; international patent publication Nos. WO 90/15816 (public Dec. 27, 1990), WO 91/13624 (public Sep. 19, 1991), and WO 93/07864 (public Apr. 29, 1993); Welistein et al. (1991) *J. Natl. Cancer Inst.* 83:716–720; and Jentsch et al. (1987) *J. Gen. Virol.* 68:2183–2192.

GAG Binding Proteins and GAG Binding Specificity

Many important regulatory proteins bind tightly to heparin, including chemokines, growth factors (including cytokines), enzymes and proteins involved in lipid metabolism. This binding property was, for a long time, thought to arise only from non-specific ionic interactions involving positively charged regions on the proteins with the negatively charged sulfates of heparin. However, recent results with two proteins, Antithrombin III (AT III) and basic fibroblast growth factor (bFGF), demonstrate that the interactions between heparin and AT III or bFGF can show specificity. The specific interaction involves complex binding sites on the protein molecule and infrequently occurring sequences in the heparin GAG chain. See, for example, EPO patent publication 0,509,517 A2, public Oct. 21, 1992; Turnbull et al., (1992) *J. Biol. Chem.* 267:10337–10341; Gallagher et al., (1992) *Glycobiology* 2:523–528; Habuchi et al., (1992) *J.Biochem.* 285:805–813; Yayon et al., (1991) *Cell* 64:841–848; and Rapreager et al., (1991) *Science* 252:1705–1708.

That specific protein binding sequences might exist in the carbohydrate chain of heparin was first suggested by the observation that some preparations were more effective than others in inhibiting coagulation. Careful studies in 1987 revealed that there is a defined five sugar sequence (pentasaccharide) with a characteristic sulfation pattern that represents the specific binding site for AT III, a protease inhibitor that blocks the action of thrombin and other enzymes which initiate blood coagulation. The Kd for the binding between AT III and this specific GAG recognition site is about 10 nM ($10^{-8}$M), which qualifies it as a high affinity interaction. Although weaker and less specific binding of these proteins to other regions of heparin can occur, virtually all of the anticoagulant activity of heparin is attributable to this five sugar sequence. This pentasaccharide, generally known as the AT III binding site, now has been synthesized chemically and shown to possess the appropriate activities of the naturally occurring sequence. Binding of antithrombin III to this site is thought to provide the basis for heparin's anticoagulant activity by positioning and "presenting" the enzyme inhibitor to the proteases thrombin and Factor Xa.

A second example of a somewhat specific binding site has been reported for basic fibroblast growth factor. This GAG sequence, isolated from fibroblast heparan sulfate, was found to represent the tightest binding fraction present. It is not clear, however, whether other molecules such as other heparin binding growth factors can bind to this sequence, nor is it clear that the affinity of this binding is as high as the binding between bFGF and heparin. The interaction between the isolated GAG sequence and bFGF might, at present, best be described then as selective, rather than absolutely specific.

Glycan binding effector macromolecules
Chemokines

Leukocytes comprise a variety of cell types which are important in health and disease. Among the leukocytes are lymphocytes which are the effector and regulator cells of the immune system, and neutrophils which are involved in chronic inflammation and immune regulation. Pharmaceutical compounds which are able to regulate this group of cells are thus important therapeutic agents. It would be of obvious interest to develop new therapeutics directed toward these targets which are more selective in their action than those currently available.

For the leukocytes to effectively exert their action they must exit the circulation, where they are normally found, and enter the tissue. Once in the tissue, they can migrate to the site, or locus, of action. In disease states, the locus may be a site of inflammation, such as an afflicted joint in rheumatoid arthritis or afflicted skin in psoriasis, or it may be an inappropriate accumulation, such as in atherosclerosis. The process of exiting from the vasculature, termed extravasation, has been proposed as a target for pharmacological intervention to inhibit the participation of selected populations of leukocytes in disease processes.

Two structurally and functionally distinct classes of adhesion molecules, selectins and integrins, are known to participate in the extravasation process. It recently has been suggested that these two classes of molecules may work in concert during extravasation. See, for example, Butcher (1991) *Cell* 67:1033–1036. The hypothesis proposes that leukocytes in the circulating blood stream become slowed and brought into intimate contact with the endothelial cells lining the blood vessels by the selecting. The force of the blood flow causes these leukocytes to roll along the endothelial surface. During juxtaposition with the endothelial cells as a consequence of the rolling process, leukocytes may become activated. Upon activation, a second group of adhesion molecules, integrins, engages counter-receptors on the endothelial surface, thus promoting a tight interaction between the leukocyte and the endothelial surface. As a result of the tight interaction, the cells are localized to the vessel lining, are no longer moved by the shear force of the blood flow, and now are able to migrate through the vessel walls out of the blood stream and into the tissue.

While the two adhesion steps of the extravasation process have been extensively investigated, the nature of the activation step has remains obscure. It has been suggested that the engagement of the E-selectin molecule may provide a trigger for activation. On the other hand, chemotactic cytokines ("chemokines") are well known to variously activate leukocytes. The class of proteins termed chemokines are structurally and functionally diverse but have in common the property of activating leukocytes by means of a class of signaling receptor, termed a G-coupled receptor. While chemokines are obvious candidates as activating molecules in the extravasation process, the manner is which they may participate remains unclear.

As a practical matter, the ability of chemokines to activate leukocytes in the extravasation process would be enhanced if they were able to be held near the endothelial surface as the leukocyte rolled along the surface. Indeed, it has been shown that chemotactic factors such as formylated peptides, complement fragments, and platelet activating factor (PAF) can be associated with endothelial cell membranes and it recently has been proposed that this interaction can occur in vivo and is critical for the activation step of the leukocyte trafficking process. This model of activation has now been extended to include chemokines. See, for example, Tanaka, et al. (1993) *Nature* 361: 79–82.

The chemokines represent a family of cell signaling factors which have closely related structures and certain common functional features, including the ability to bind heparin. To date 15 member molecules have been identified (see Table I, infra.) Among the better characterized chemokines are Platelet factor 4 (PF4) and Interleukin 8 (IL8).

PF4 was originally identified on the basis of its ability to bind to heparin. While the structural characteristics of this protein are well characterized, its physiological role remains obscure. It is known that PF4 can neutralize heparin's anticoagulant activity by binding to heparin. Because other chemokines also can interact with heparin, it is possible but not proven, that other members of the chemokine family can also neutralize heparin. It has been suggested that PF4 may provide a natural regulatory effect for coagulation by binding to heparan sulfate on the endothelial cell surface but, to date, such binding has not been directly demonstrated in vivo.

Although PF4 does not have significant demonstrable effects on leukocytes, many of the other chemokines appear to be intimately involved in the trafficking of these cells. It has been proposed that these factors play an important role in the normal maintenance of the immune system and participate in a number of pathological conditions, such as inflammatory disturbances, autoimmune disorders, sepsis and atherogenesis. See, for example, Oppenheim, et al. (1991) *Annu. Rev. Immunol.* 9:617–648. Consistent with this concept, the chemokines have been shown to be somewhat selective attractants and activating factors for various subtypes of leukocytes. For example, IL-8 is a potent attractant and activator for neutrophils and possibly a certain lymphocyte subset but has no detectable activity on monocytes. By contrast, MCP-1 is a potent chemoattractant for monocytes but displays no known activity on neutrophils. Other members of the family have partially specific but often overlapping activities and presently it is not clear how specific signaling of these proximal leukocyte mediators may be mediated. As chemokines are direct stimulators of critical subtypes of immune and/or inflammatory cells, they represent important targets for the development of pharmacological compounds which specifically inhibit or modify the action of chemokines.

From a functional standpoint, the best characterized chemokine is IL-8. Based on the conserved structural and functional features of members of the chemokine family, it is expected that the mechanism of IL-8 action will serve as a model for other members of the chemokine family which are produced in the parenchyma, either by parenchymal cells or by leukocytes that have extravasated to sites within the tissue. While IL-8 can be produced by a variety of cell types within the parenchyma, it also can be produced by certain activated leukocytes. In vivo, production of chemokines in leukocytes is likely to be a secondary event, occurring after the leukocytes have entered sites of inflammation and have become activated.

The expression of IL-8 and the means by which it acts to attract neutrophils has been studied both in vitro and in vivo. Endothelial cells in culture are reported to produce and localize IL-8 when stimulated with proinflammatory factors. Moreover, studies involving skin tissue show that exogenously added IL-8 can preferentially associate with certain regions within the microvascular endothelium. It also has been proposed, based on in vitro data, that neutrophils preferentially traverse a gradient of IL-8 associated with the substrate (i.e. a haptotactic gradient rather than chemotactic gradient). Accordingly, it is possible that part of the chemokine mechanism of action is by means of localization to a cell surface and creating a gradient across which activated leukocytes can migrate.

Finally, another member of the chemokine family MIP 1β, has been shown to bind to both heparin-BSA conjugates and a leukocyte derived proteoglycan, CD44. Binding to these molecules under the experimental conditions employed led to an enhancement of the ability of MIP 1β to activate lymphocytes. It is possible, therefore, that the functional form of MIP 1β in vivo is bound to proteoglycans, although the actual molecule or molecules for specific attachment remain unknown. MIP 1β also has been shown to be associated with endothelial cells within the lymph nodes in vivo, possibly by means of a cell surface proteoglycan.

While IL-8 has been well established as a stimulator of neutrophils, it also has been reported to have anti-inflammatory action. In the reports, however, IL-8 was injected directly into the bloodstream, producing a concentration gradient inverse to that occurring under physiological conditions, and one likely to have significant adverse consequences in therapeutic applications. It would be desirable to improve upon this with a specific antagonist of the action of individual chemokines.

Growth Factors/Cytokines

It is well recognized that the endogenous hetero-oligodisaccharides heparan sulfate and heparin bind with appreciable affinity to a wide spectrum of the mitogenic proteins termed cytokines and growth factors, although the strength of these interactions varies considerably among the different factors. Among the growth factors and cytokines described as heparin/HS-binding proteins are: TGF-β, endothelial cell growth factor, IL-3 and GM-CSF, interferon-γ, hepatocyte growth factor, fibroblast growth factor (FGF) family [FGF-1 (acidic FGF), FGF-2 (basic FGF), FGF-3 (int-2), FGF-4 (Hst-1, K-FGF), FGF-5, FGF-6 (Hst-2) and FGF-7 (keratinocyte GF). For example, heparin will release TGF-β from inactive complexes with $\alpha^2$-macroglobulin and will potentiate TGF-β action. The stability in solution of acidic and basic FGF (aFGF and bFGF) is enhanced in the presence of HS/heparin, and the polysaccharides potentiate the mitogenic activity of the FGFs, especially of aFGF. These effects are presumed to be due to the formation of complexes between FGF and heparin which prolong the biological lifetime of the proteins by protecting them from proteolysis and thermal denaturation. In tissues, aFGF and bFGF can be detected in the extracellular matrix and basement membranes, where they are bound to HS. It has been proposed that the action of heparinases or proteases that degrade heparan sulfate proteoglycans will release FGFs from the basement membranes enabling them to act on nearby target cells. In addition to effects on FGF stability and tissue localization, a central role has now been described for HS in controlling the interaction of bFGF with cell signaling receptors.

Lipoproteins

Several important proteins of lipid metabolism are known to bind heparin and to be regulated by this interaction. One example is lipoprotein lipase, an extracellular enzyme which is able to initiate and facilitate the process of cellular uptake of blood lipids in several ways (Olivecrona, T. and Bengtsson-Olivecrona, G. (1987), Lipoprotein Lipase, (Borenszajn, J. ed.) pp. 15–58 Evener Publishers Inc., Chicago). The activity of this enzyme appears to be regulated by binding to heparan sulfate on the cell surface and in the extracellular matrix (Williams et al., (1992) *J. Biol. Chem.* 267: 13284). Current thinking holds that this binding interaction is quite non-specific in nature as it may be competed by the addition of either heparan sulfate or dermatan sulfate which are structurally distinct polyanionic polysaccharides (Saxena et al. (1992) *J. Biol. Chem.* 268: 14812). Other proteins involved in lipid metabolism such as, for example, two subunit proteins of blood lipid transport complexes, apolipoprotein B and apolipoprotein E, also are known to bind to heparin and heparan sulfate and cellular uptake may be regulated by this interaction (Ji et al. (1993) *J. Biol. Chem.* 268: 10160). This binding also is suggested to depend on non-specific, ionic interactions (Radhakrishnamurthy et al. (1990) *Eur. Heart J.* 11, Suppl. E, 148). Finally, high affinity binding of LDL to its receptor, which is required for internalization of the complex, may be facilitated by initial interaction with cell surface heparan sulfate.

Amyloid Proteins

Amyloid diseases are caused, in part, by the self-association of amyloid protein to form insoluble fibrillar complexes within and around cells thereby impeding normal cellular function. Recent studies have shown that glycosaminoglycans, likely associated with the extracellular matrix, especially heparan sulfate (Buee et al. (1993) *Brain Res.* 601: 154) and chondroitin sulfate (DeWitt et al. (1993 *Exp. Neurol.* 121: 149), colocalize in these amyloid aggregates and it has been suggested that glycosaminoglycans participate directly in the formation of amyloid fibril formation (de Beer et al. (1993) *J. Biol. Chem.* 268: 20606). Drugs which are able to selectively block the association of amyloid proteins may be expected to provide prophylactic and/or therapeutic benefit in a variety of amyloidoses, for example, Alzheimers Disease, inflammatory amyloidoses, and prion diseases.

Selectins

Selectins are leukocyte adhesion molecules involved in the first step of leukocyte extravasation. Three selectins are known to exist, L-selectin (leukocyte), P-selectin (platelet), and E-selectin (endothelial cell). L-selectin appears to be exclusively found on leukocytes, while both E and P selectin are found on endothelium and elsewhere. The molecules or counter-receptors on the surface of a neighboring cell which are specifically bound by selectins during the process of adhesion have not been fully characterized although selectins have been shown to bind to oligosaccharide structures, especially sialyl Lewis X (Polley et al. (1991) *Proc. Nat. Acad. Sci., USA* 88: 6224). More recently, binding to sulfated sugars, including GAG structures, has been reported (Lasky et al. (1992) *Cell* 69: 927, Fiezi, T. et al. (1993) *J. Cell Biochem. Supp.* 17A:372, and Norgard et al. (1993)

*FASEB Journal* 7: A1262). Selectins appear to be an example of an effector protein in which the binding of the glyceptor is the primary effector function of the molecule. Serum soluble glyceptor analogs which are specific for one or more selectins may be expected to prevent the first step of leukocyte adhesion, thereby abrogating an inflammatory or immune response.

It has not been previously demonstrated or predicted that the interaction between the vast majority of glycan-binding proteins and surface-immobilized GAG chains can show any degree of specificity. The unanticipated discovery of such specificity now enables the development of a kind of inhibitory molecule, not previously envisioned, that can specifically antagonize the action of a given glycan-binding protein. For example, one now can specifically antagonize the action of a given chemokine or growth factor without affecting significantly the action of the remaining members of the protein family. Moreover, the discovery now enables the development of analogs of specific glycosaminoglycan sequences that can act as agonists or have other utilities in vivo including, for example, as imaging or other tissue-targeting agents.

Provided herein is an enabling description of the fundamental discovery and resulting concept which permits the identification of such therapeutically useful compounds. Also provided are an enabling description of a process for identifying and isolating the full range of specific GAG binding sequences and an enabling description of a process for utilizing such sequences to screen for therapeutically useful compounds, as well as a description of the characteristics defining useful natural source-derived or synthetically produced analogs, including those that act as antagonists to the protein-glycan interaction.

It is an object of this invention therefore to provide means for modulating a biological effect induced by a glycan-binding protein-receptor or glycan-binding protein-protein interaction by modulating, including preventing or otherwise interfering with, the interaction between a glycan-binding effector protein and the glycan sequence that binds it. Another object is to teach a method for identifying and isolating analogs of a glycan sequence having specificity for a given glycan-binding protein, and to teach the use of these analogs as agonists or antagonists. Still another object of the invention is to provide means for controlling specific aspects or components of undesirable inflammatory or immune responses without inhibiting or otherwise adversely affecting beneficial aspects or components of the response. Yet another object is to provide means for controlling undesired cell growth and proliferation, or to modulate lipid metabolism or its effects in vivo. Another object of the invention is to provide means for therapeutic and prophylactic manipulation of chemokine, cytokine, enzyme, growth factor and related biological molecule function, including providing novel compositions, and providing a process for discovering useful novel compositions. Such compositions have utility for altering pathologic responses by inhibiting or enhancing the action of one or more members of any of the group of proteins set forth above. The useful compositions contemplated by the invention also include novel tissue targeting agents having general utility.

These and other objects and features of the invention will be apparent from the description, drawings and claims which follow.

SUMMARY OF THE INVENTION

It now has been discovered that the activity of glycan-binding proteins, including growth factors, chemokines, cytokines, and a host of other biological or "effector" proteins, is modulated by the interaction of these proteins with specific, determinable oligodisaccharide structures ("glycans") pendant from proteoglycans immobilized on a cell or extracellular surface. The specific binding between the glycan-binding protein and the oligodisaccharides is determined by the structure and sequence of saccharides, typically disaccharides, and usually including the sulfation pattern defined within the oligodisaccharide unit, all of which together define a binding site having relatively high affinity and specificity for a given glycan-binding protein. These oligodisaccharide surface-immobilized binding sites differ from true cell surface receptors in that they typically lack the transmembrane signaling function associated with ligand-receptor binding and, typically, bind to a site on the protein different from that recognized by the receptor binding site. This new observation presents an opportunity for modulation and control of the physiological function of the glycan-binding protein.

As used herein, "glycan-binding protein" refers to all proteins having a binding site for a specific, determinable sequence in a glycosaminoglycan immobilized on a surface, including a cell or extracellular matrix surface. The term includes both proteins which also interact specifically with other proteins to induce a biological effect in vivo, (so-called "effector" proteins), as well as proteins whose primary action is by glycan interaction. Such proteins include, for example, surface-bound selectins, which are believed to enhance intimate contact of migratory cells to a tissue surface by interaction with glycans on the surface of a migratory cell.

As used herein, "effector proteins" define glycan-binding proteins capable of inducing a biological effect in vivo by binding specifically to another protein. For example, the effector protein may bind a cell surface receptor, thereby inducing a transmembrane effect that subsequently induces a cellular effect. Alternatively, the effector protein may catalyze hydrolysis of another, inactive protein to convert it to its active form. The effector proteins important to the instant invention all also have two binding sites, one specific for a glycan sequence, and one specific for interaction with another, typically different protein.

Accordingly, in one aspect, the invention provides a method for modulating the interaction between a ligand and its "Glyceptor" sequence. As used herein, the term "Glyceptor" sequence refers to an oligodisaccharide sequence, including sulfated disaccharides, contained within a given glycosaminoglycan immobilized on a cell or extracellular matrix surface and which binds, with specificity, to a glycan-binding protein. Thus, as used herein, "Glyceptor" sequence and "protein-specific glycosaminoglycan sequence" are used interchangeably and are understood to be synonyms. The molecular surface structure on the glycan-binding protein that interacts specifically with a given "Glyceptor" sequence is referred to herein as a "glycan-binding site."

In one embodiment, the glycan-binding protein is an effector protein that also partakes in a ligand-receptor interaction, or other protein-protein interaction having a regulatory or other physiological effect in the body. Typically, the "Glyceptor" sequence-effector protein interaction alone has no transmembrane 14 signal transducing or other direct effect. Without being limited to any given theory, interaction of a given glycan-binding effector protein with its "Glyceptor" sequence serves to enable, or otherwise enhance, the ability of the ligand to interact with its receptor or other protein. The ligand-receptor or other protein-protein interaction may occur on the same cell surface to which the "Glyceptor" sequence is immobilized, may occur on an adjacent cell, or may occur on an extracellular matrix surface. Examples of useful "Glyceptor" sequence binding effector proteins that also partake in ligand-receptor interactions include growth factors, cytokines, chemokines, complement factors, and the like. Examples of useful "Glyceptor" sequence binding effector proteins that also partake in other protein-protein interactions include enzymes and transport proteins such as those involved in lipid metabolism.

Thus, in one aspect, the method of the invention comprises the step of substantially preventing or otherwise interfering with the interaction of a glycan-binding effector protein of interest with its "Glyceptor" sequence. By interfering in some way with the interaction between the glycan-binding effector protein and its "Glyceptor" sequence, one effectively interferes with the ability of the protein to interact with its receptor or other protein. The step of substantially preventing or otherwise interfering with the interaction of the glycan-binding effector protein with its "Glyceptor" sequence may be achieved by administering to an animal a molecule that acts as a "Glyceptor" sequence analog ("'Glyceptor' sequence antagonist"), and which competes with the "Glyceptor" sequence for ligand binding. The "Glyceptor" sequence antagonist may act by preventing the protein from interacting with its "Glyceptor" sequence, and/or by competitively displacing a protein from its "Glyceptor" sequence "seat". Useful "Glyceptor" sequence antagonists contemplated by the invention include soluble forms of the "Glyceptor" binding sequence, or any other synthetic or natural-sourced sequences that constitute or functionally mimic the structure of the "Glyceptor" sequence, and which have a specific, predetermined composition.

In one preferred embodiment, the invention provides methods for modulating the inflammatory response in an animal by inhibiting circulating leukocytes from becoming activated on the endothelial luminal surface and entering the tissue to act at a site of inflammation, immune cell stimulation, or regulation. As described herein, migrating leukocytes come into intimate contact with the endothelial luminal surface, in part by association with one or more selectins on the endothelial luminal surface. Chemokines are secreted to the luminal surface when an inflammatory or immunomodulatory response is triggered, and "Glyceptor" sequences pendant from the luminal surface present the chemokines to adjacent leukocytes. The presented chemokines then can bind to receptors on the "tethered" leukocyte cell surface, triggering activation of the leukocytes and extravasation. By the method of this invention, it now is possible to (1) prevent presentation of the chemokines and/or, in a preferred embodiment, (2) to remove secreted chemokines from the luminal surface, thereby preventing leukocyte activation and consequent migration into the tissue. The methods are anticipated to be particularly useful in the treatment of acute inflammation such as is caused by trauma, septic shock, and other conditions of systemic inflammatory response syndrome (SIRS) and in the treatment of chronic inflammation, including rheumatoid arthritis, psoriasis, inflammatory bowel disease and the like, as well as other autoimmune disorders and immune dysfunction. In an alternative method it also is anticipated that one can inhibit or interfere with leukocyte tethering by modulating the selectin-glycosaminoglycan binding interaction (see below.)

In another preferred aspect, the invention provides a method for modulating the biological effect induced by a glycan-binding growth factor or other cytokine by interfering with, or otherwise preventing interaction of, a given growth factor with its "Glyceptor" sequence which may be on the same cell as the growth factor receptor, a neighboring cell, or the extracellular matrix. The method is anticipated to be particularly useful in inhibiting undesired cell proliferation, such as can occur in a hyperproliferative disease, including cancers or atherosclerosis.

In yet another aspect, the invention provides a method for modulating lipid metabolism, for example by modulating the interaction of glycan-binding lipolytic enzymes and other molecules involved in lipid metabolism with their specific "Glyceptor" sequences on cell or extracellular matrix surfaces. Specifically, the present invention provides a basis for recognizing and characterizing the specificity of the interactions of glycan-binding effector lipoproteins with surface-bound glycans, and enables the discovery of novel therapeutic agents which can act by, for example, selectively blocking the binding of lipoprotein lipase to cell surfaces, thereby reducing the accumulation of lipid in blood vessel walls. Such therapeutic agents may be expected to have utility in the treatment and prophylaxis of atherosclerosis. Specific inhibitors of lipid transport proteins may have utility in lowering blood lipid levels.

In still another aspect, the invention provides therapeutics having utility in treating amyloidoses, by selectively blocking the association of amyloid proteins with cognate glycosaminoglycan chains.

In another embodiment, the glycan-binding protein has no second binding site for interaction with another protein to induce a biological effect. Rather, the primary action of the protein appears to be by interaction with a glycosaminoglycan. Examples of such proteins include the selecting, a class of proteins typically immobilized to a tissue surface whose action is to enhance the "tethering" or intimate contact of a migrating cell to the tissue surface. The action is believed to occur by binding to glycosaminoglycans on the migrating cell surface. Modulation of this interaction, by means of a "Glyceptor" sequence analog or a soluble selectin analog may be useful, for example, in interfering with extravasation, and modulating thereby progress of an inflammatory response.

Thus, in another aspect, the method of the invention comprises the step of interfering with the normal interaction of a non-effector glycan-binding protein with its "Glyceptor" sequence. For example, a "Glyceptor" sequence analog may be administered to a mammal which interacts specifically with a given selectin, thereby blocking the ability of this protein to interact with a migratory cell. In another aspect, "Glyceptor" sequence analogs may be used to target an agent, e.g., an imaging or therapeutic agent, to a surface-bound glycan-binding protein such as a selectin immobilized on the endothelial luminal surface.

Alternatively, a molecule may be administered that is a glycan-binding protein analog ("ligand antagonist" or "decoy ligand") which competes with the glycan-binding protein for "Glyceptor" sequence binding and, when bound, prevents or substantially inhibits the protein from binding to the "Glyceptor" sequence, and/or competitively displaces protein from its "Glyceptor" sequence. Useful such glycan-binding protein antagonists include antibodies recognizing one or more epitopes on the "Glyceptor" sequence and capable of blocking or otherwise interfering with the ligand binding site on the "Glyceptor" sequence. In one preferred embodiment, useful ligand antagonists include modified, soluble forms of a glycan-binding effector protein of interest which can still bind the "Glyceptor" sequence with specificity but which, as modified, can not interact with the other protein or receptor necessary for effecting the biological activity in vivo. Ligand antagonists, including the modified glycan-binding effector protein, have an additional utility as in vivo targeting agents. For example, an imaging or cytotoxic agent can be complexed with the modified glycan-binding protein using standard means, such as by covalent attachment, and be targeted to the site of action of the ligand thereby. Methods for creating target-specific complexes are well-known and are well described in, for example, the cancer therapeutic art. Still other useful ligand antagonists include synthetic organics defining a molecule capable of mimicking the glycan binding site on the ligand.

In yet another aspect, the invention provides isolated complexes of noncovalently bound glycan-binding proteins and "Glyceptor" sequences, including synthetic "Glyceptor" sequence analogs, and therapeutic compositions using these complexes. For example, in one embodiment, the complex can provide a means for protecting a glycan-binding protein to be administered to a mammal from degradation.

In still another aspect the invention contemplates a chimeric synthetic molecule comprising at least two "Glyceptor" sequences covalently linked and having a conformation sufficient to allow concurrent binding of each said protein-specific glycosaminoglycan sequence to a specific glycan-binding protein. Preferably, each protein-specific glycosaminoglycan sequence binds to a different protein-specific glycosaminoglycan binding site. The two binding sites may be tethered by means of a linker capable of acting as a spacer as well as a crosslinking means. Preferably, the linker also allows free rotation of the two sites independent of one another. The chimeric molecule is anticipated to have particular utility as an agonist functioning, for example, to help present a glycan-binding effector protein to a receptor, by binding both a soluble effector protein and a surface bound protein.

In one currently preferred embodiment, the "Glyceptor" sequence analogs of the invention useful as antagonists and agonists have a binding affinity for the ligand of interest defined by a dissociation constant in the range of $10^{-6}$M to $10^{-12}$M, preferably having a dissociation constant of less than $5 \times 10^{-6}$M, more preferably less than $10^{-7}$M, or even $10^{-8}$M. As will be appreciated by those skilled in the art, the higher the binding affinity of the analog, the lower the concentration needed to induce a therapeutic effect in vivo, and the less likely the molecule is therefore, to induce a toxic response.

In another preferred embodiment, the overall length of the "Glyceptor" sequence analog preferably does not exceed about 40 Å, and preferably is less than 40 Å, on the order of about 15–20 Å. Where the isolated "Glyceptor" sequence or an analog to be used comprises an oligodisaccharide sequence, the molecule preferably has fewer than 20 monomer units, preferably fewer than 16 monomer units, most preferably between 4–15 units, inclusive. Smaller oligodisaccharide sequences may reduce specificity and larger sequences may enhance toxicity. Preferred oligosaccharide antagonists also have an overall length of less than 40 Å. In all cases, the oligodisaccharide analogs contemplated have a specific, predetermined composition, which serves to distinguish the compositions of the invention from the endogenous soluble heterogenous oligosaccharide mixtures that may be found in the body.

Non-oligodisaccharide molecules useful as "Glyceptor" sequence analogs include antibodies or other peptides capable of interacting specifically with the "Glyceptor" sequence binding site on the glycan-binding protein. Still another useful class of molecules includes synthetic organic molecules whose chemical structure functionally mimics that of a "Glyceptor" sequence in binding specifically with a glycan-binding protein. These synthetic constructs may or may not include carbohydrate and amino acid sequences. For example, suramin, a polysulfonated naphthylurea, interferes with "Glyceptor" sequence-effector molecule interactions, presumably by competing with the "Glyceptor" sequence for the ligand binding site. Here, the naphthylurea likely provides a scaffolding or backbone structure with an appropriate distribution of sulfonates disposed about the heterocyclic rings to functionally mimic the sulfated oligodisaccharide sequence that defines the protein-specific glycosaminoglycan sequence. Thus, other synthetic organics can be generated having unique backbone structures, and on which are disposed constituents of appropriate charge and size. However derived, the "Glyceptor" sequence analog preferably has an appropriate distribution of functional substituents capable of interacting specifically with the glycan binding site. For synthetic organics, the appropriate substituents may be provided by pendant carboxylates, phosphates, sulfonates, hydroxylates, amino groups, alkyl and aromatic moieties.

In a particularly preferred embodiment, the synthetic organic "Glyceptor" sequence antagonist is derived from the class of molecules whose structure is based on features of the glycan binding site on the ligand with which the glycan analog interacts, the characteristics of the class being defined by the generic structure as described in detail herein below. As will be appreciated by those having ordinary skill in the art of chemical synthesis, a combinatorial library can be constructed containing multiple candidate sequences created based on the generic structure, and the candidates tested in the screening assay presented herein to identify useful analogs, including antagonists, having appropriate affinity for a ligand. Similarly, a combinatorial library "kit" can be constructed comprising isolated, captured candidate molecules defined by the generic structure, a preselected glycan binding protein of interest, and a means for screening the candidates for their ability to bind said glycan binding protein with an affinity above a preselected threshold level.

Thus, in still another aspect, the invention provides a method for identifying specific oligodisaccharide sequences and functional analogs thereof which interact specifically with glycan-binding proteins, including chemokines, cytokines and other effector molecules involved in regulation of the immune/inflammatory response. As described herein, selected oligodisaccharide sequences having a defined pattern of charged groups and a desired binding specificity and affinity for a given ligand may be identified and used to create serum-soluble "Glyceptor" sequence analogs, useful per se, or as screening reagents or templates for the rational design of polypeptide or organic-based "Glyceptor" sequence analogs. In still another aspect, the invention provides a high flux screening assay for identifying candidate analog molecules.

In yet another aspect, the invention provides a means for site-specific delivery of therapeutic or diagnostic agents to localized regions of the vasculature. As described herein, vascular selectins such as P or E selectin can bind to "Glyceptor" sequences. Therefore, "Glyceptor" sequences and analogs thereof, especially those which are directed toward P or E-selectin, may be used to deliver agents in a preferential fashion to the vascular endothelium of inflamed tissue in order, for example, to permit imaging of sites of inflammation or tumor growth. Alternatively, drugs which are cytotoxic or antiproliferative may be delivered to provide a desired effect, for example, the inhibition of angiogenesis.

BRIEF DESCRIPTION OF THE DRAWINGS

The foregoing and other objects of the invention, the various features thereof, as well as the invention itself, may be more fully understood from the following description, when read together with the accompanying drawings, in which:

FIG. 1A–1C are schematic representations of the mechanism of action of drugs produced and used in accordance with the invention, to modulate the binding of effector chemokines to an epithelial cell surface.

FIG. 10B graphs the inhibitory effect of 25 different polysulfonated naphthylurea compounds on PDGF- "Glyceptor" sequence binding.

DETAILED DESCRIPTION

The invention essentially consists of compounds which are selected for their ability to mimic a specific "Glyceptor" sequence-glycan-binding protein interaction, and methods for their selection and use. In one embodiment the compounds specifically inhibit the interaction of a ligand with its cognate binding sequence in a glycosaminoglycan chain, and have particular utility for inhibiting that interaction in vivo. FIGS. 1 and 2 illustrate one mechanism of the compounds provided by the invention, as it pertains to chemokine-"Glyceptor" sequence interaction (FIG. 1) and growth factor-"Glyceptor" sequence interaction (FIG. 2), and where the "Glyceptor" sequence is cell surface-bound sequence. The invention also is anticipated to be useful for effector glycan-binding protein-"Glyceptor" sequence interactions where the "Glyceptor" sequence is bound to an extracellular matrix surface.

Figure 1A:
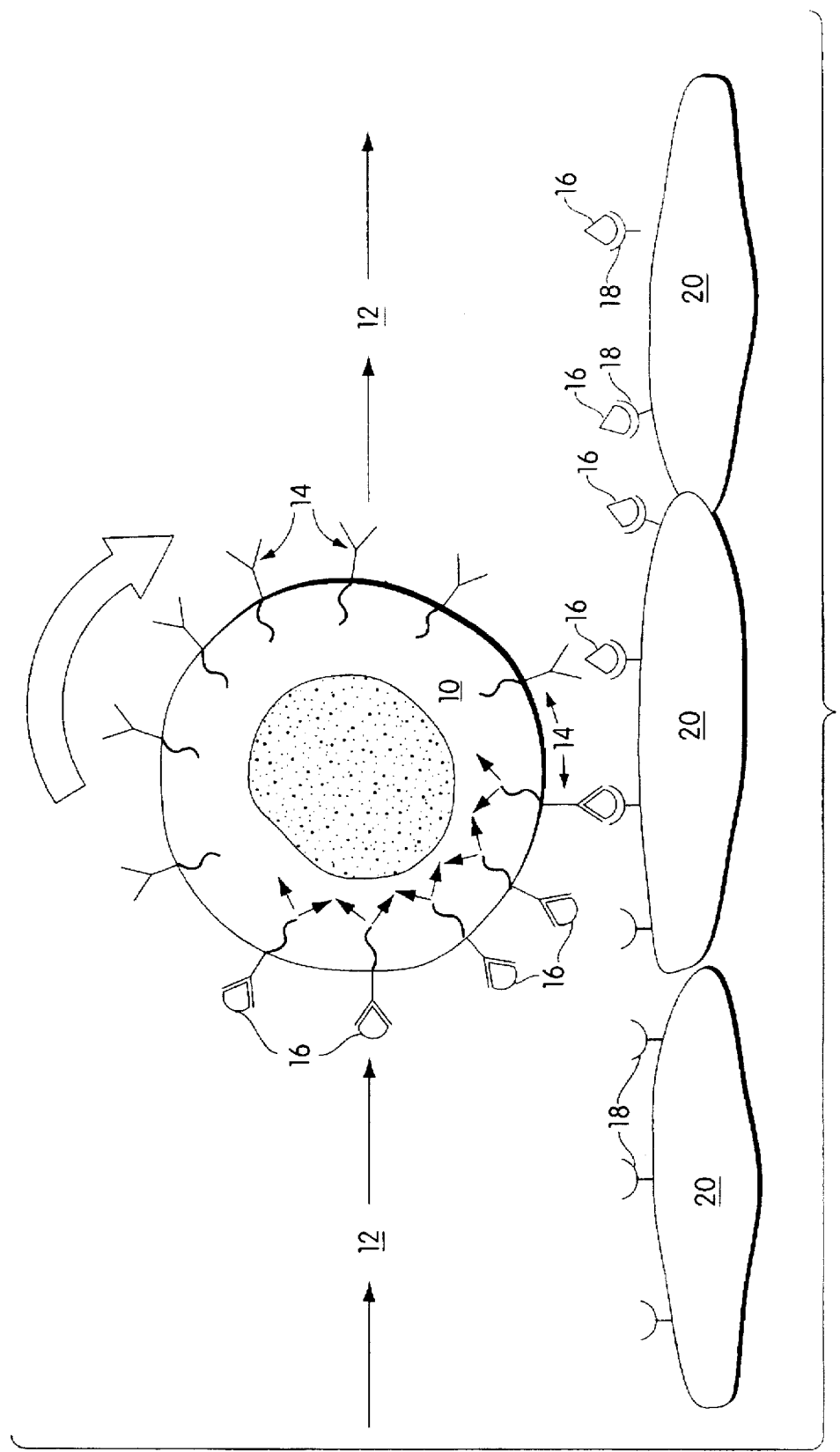

FIG. 1A depicts a leukocyte 10 within the lumen of a capillary 12. The leukocyte has transmembrane receptors 14 which bind to, e.g., ligands such as chemokines, 16. The binding results in transduction of signal across the membrane of the leukocyte 10 and stimulation of mechanisms that lead to cell activation and tight binding to the endothelium, thus initiating migration into the tissue. The chemokines 16 are presented by "Glyceptor" sequences 18 pendant from and fixed to proteoglycans embedded in the membranes of the endothelial cells 20 which line the capillary. The leukocyte 10 rolls along the endothelial cell surface, carried by the blood flow.

FIG. 1B depicts the mode of action of "Glyceptor" sequence antagonists in interrupting the process illustrated in FIG. 1A. As shown, serum-soluble "Glyceptor" sequence antagonist molecules 25 competitively displace chemokine molecules 16 from the "Glyceptor" sequences 18, carrying the chemokines away in the blood flow as "Glyceptor" sequence antagonist-chemokine complexes 26, and preventing activation of eukocyte 10.

Figure 1C:
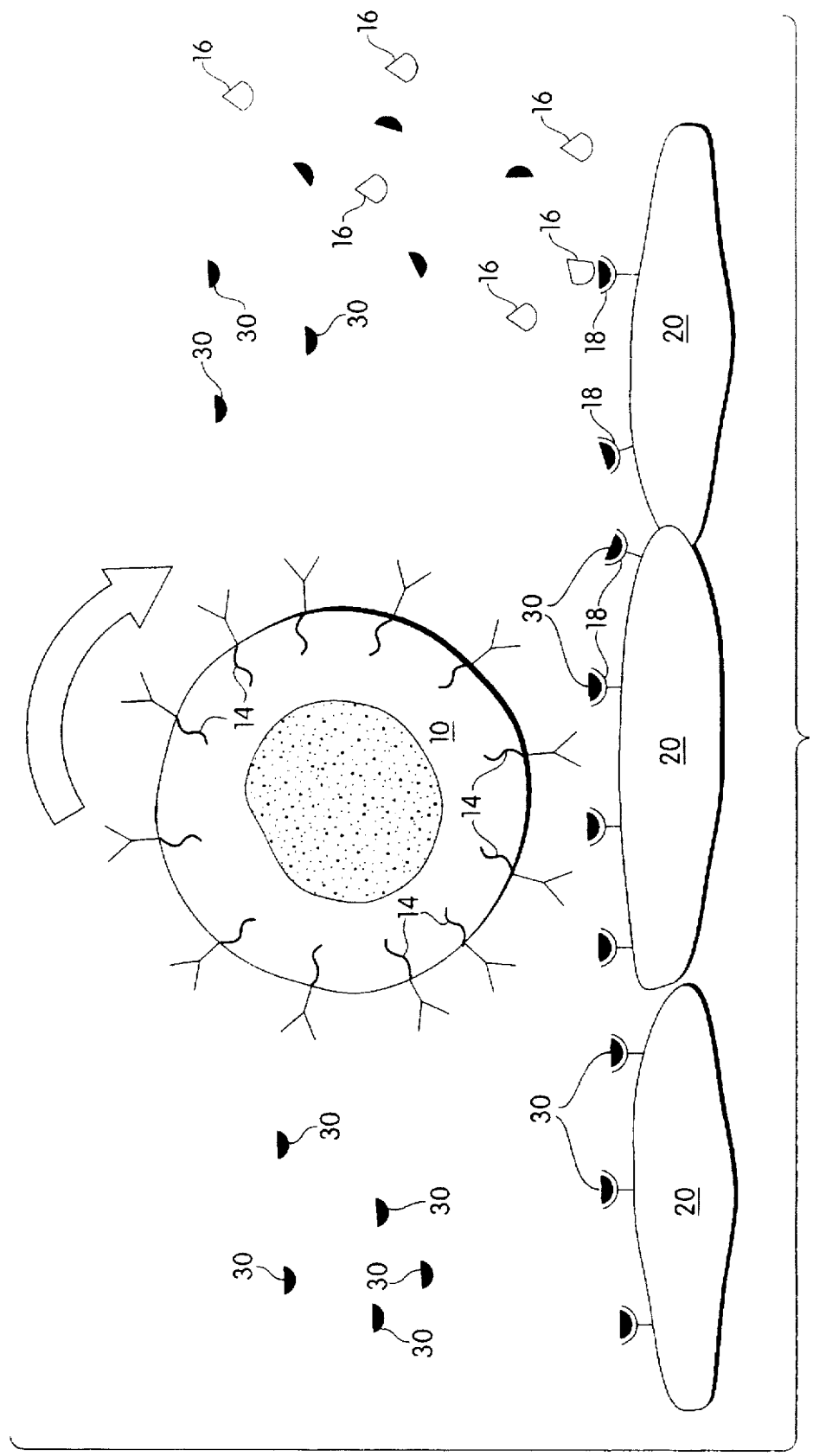

FIG. 1C depicts still another mode of action, this time using ligand antagonist of the type described herein. In this case chemical species, here numbered 30, the ligand antagonist, which mimic the portion of the ligand which binds to the "Glyceptor" sequence 18, compete with and displace chemokine 16 off of the "Glyceptor" sequence 18. The chemokines 16 again are swept away, interfering with activation of leukocyte 10.

In still another mode of action, a "Glyceptor" sequence antagonist can interfere with leukocyte activation by specifically binding to a surface-bound selectin, thereby preventing the selectin from interacting with the migrating leukocyte.

Figure 2A:
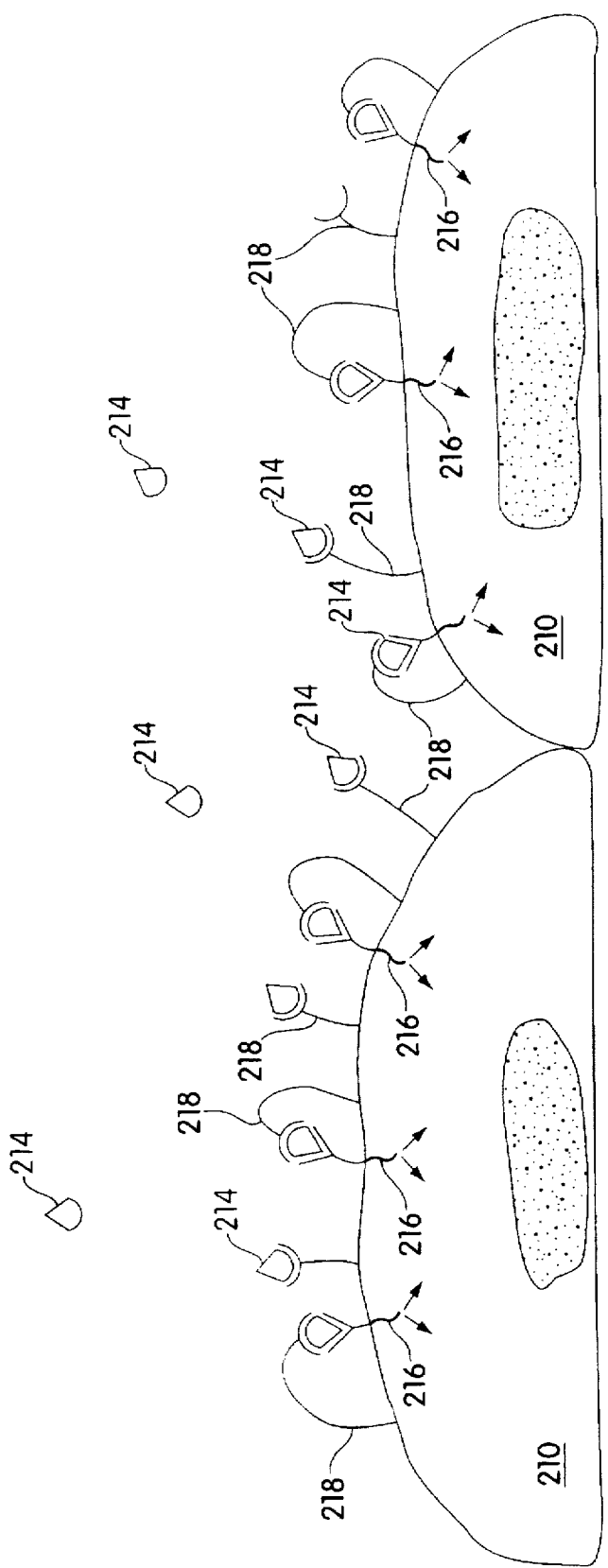
FIG. 2A–2C schematically illustrate a related mechanism of action of drugs produced in accordance with the invention to modulate the binding of a given effector growth factor to a cell surface "Glyceptor" sequence.
Figure 2B:
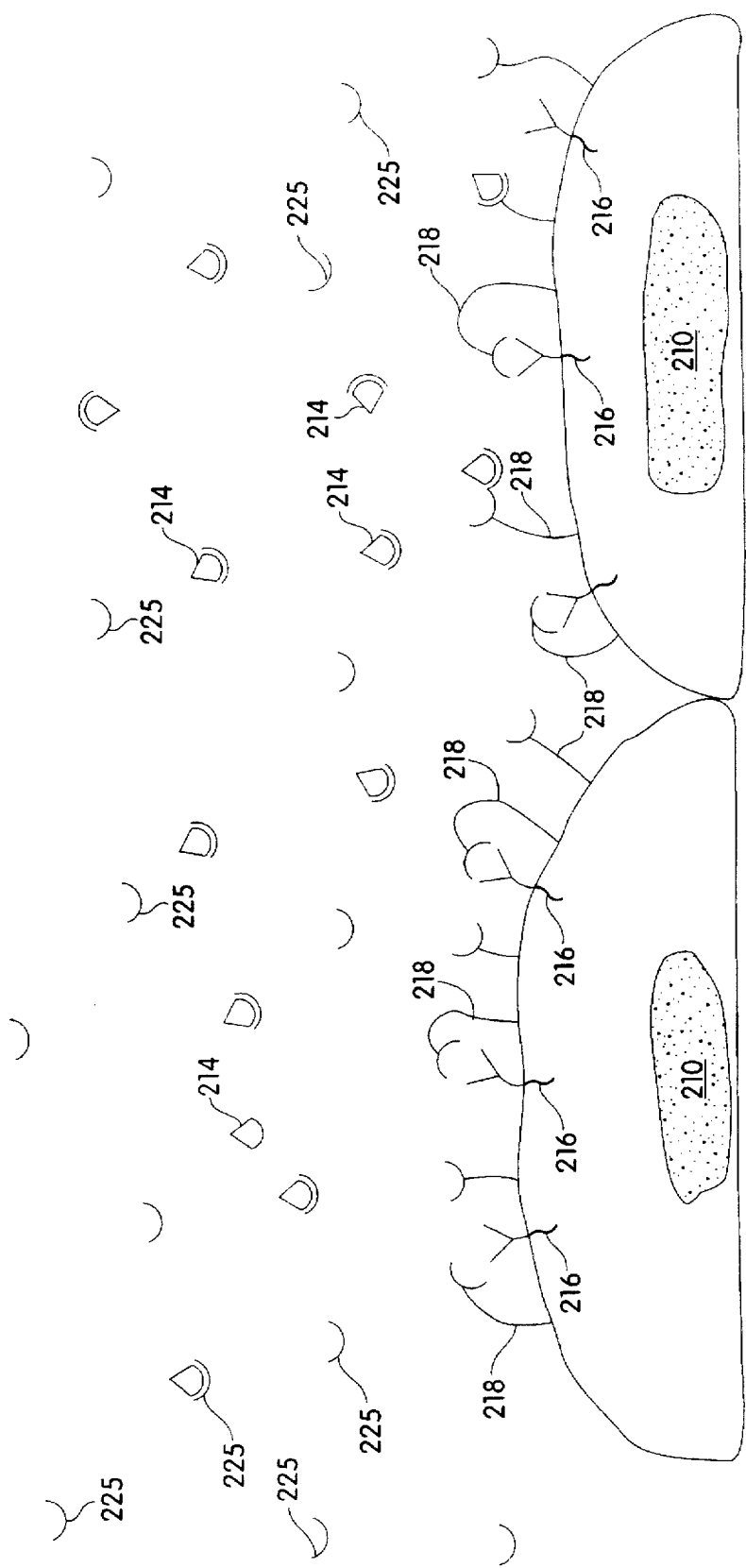
Figure 2C:
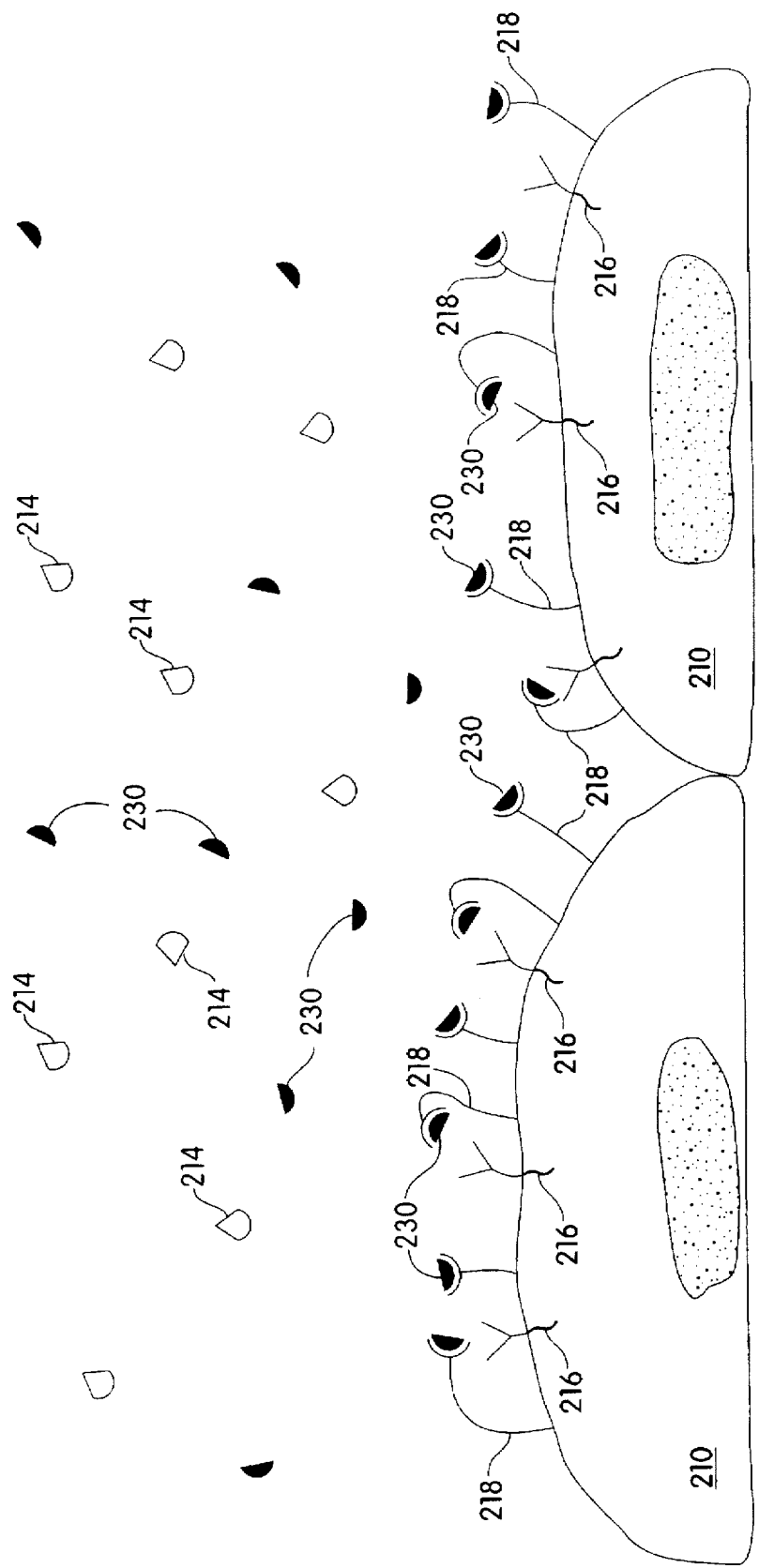

FIG. 2A shows cells 210 having both "Glyceptor" sequences 218 and transmembrane receptors 216 on their surfaces. Growth factor molecules 214 are aided in binding to receptors 216 by "Glyceptor" sequences 218, analogous to a "Glyceptor" sequence "hand" guiding a growth factor "key" into a receptor "lock" to activate cell proliferation through a transmembrane signal. In FIG. 2B "Glyceptor" sequence antagonists 225 are reacting in a solution with growth factor 214 and competitively stripping off growth factor bound to "Glyceptor" sequences 218 to modulate (here diminish) the activity of the growth factor 214 on the cells 210. FIG. 2C shows ligand antagonists 230 similarly modulating growth factor activity.

The instant application also provides a novel process for selecting useful analogs of the glycan-binding protein-"Glyceptor" sequence interaction from a collection of randomly obtained or rationally designed candidate compounds. In one aspect, compounds which are selected by the process described herein will have the useful property of specifically displacing glycan-binding proteins, including biologically active effector proteins such as chemokines, cytokines and growth factors, from their functionally active locations. In the case of chemokines this includes displacement from the endothelial lining of the vasculature and other cell surfaces. Selective displacement of these bioactive chemokines from GAG binding sites on the endothelium, for example, negates their activity, thereby providing therapeutic benefit, in two ways: 1) they are no longer available for activation of their target leukocytes that are brought into proximity with the endothelial-presented chemokines during periods of inflammation or immune stimulation; and 2) their displacement results in rapid removal by the circulation from the distressed area. As a consequence, the pathologic effect of the chemokine is greatly reduced or prevented altogether.

Similarly, where the effector molecule is a growth factor, use of the antagonists of the invention can interfere with, for example, undesired cell growth. In the case of FGF, for example, a growth factor implicated in cancer and angiogenesis, use of the antagonists may be used to prevent tumor growth. In the case of PDGF-HF and HBEGF, growth factors implicated in restenosis, "Glyceptor" sequence antagonists may be used to inhibit smooth muscle cell proliferation.

Where the glycan-binding protein is a selectin, useful "Glyceptor" sequence analogs of the invention can interfere with undesired cell-cell interaction.

Useful "Glyceptor" sequence analog compounds of the invention may include antibodies or other related molecules capable of interacting and interfering with ligand-"Glyceptor" sequence interaction by binding the ligand. Antibodies can be made by standard means well known and described in the art (see, for example, *Immunology*, Roitt et al., eds. Harper and Row, New York, 1989) using an isolated oligodisaccharide "Glyceptor" sequence of interest as the antigen.

Other useful "Glyceptor" sequence analogs include soluble forms of GAG oligodisaccharides or may be derived from the endogenous cognate GAG binding sequences. Alternatively, the analog may be a mimetic compound of the cognate GAG sequence, including a non-carbohydrate mimetic compound. Briefly, the "Glyceptor" sequence analog compositions obtained through this enablement may be sulfated glycosaminoglycan oligodisaccharides of a predetermined, defined sequence, including that of a "Glyceptor" sequence found in nature, or they may be synthetic mimetics thereof. A process is provided herein for the selection of such suitable compounds.

The synthetic organic analog molecules useful in the invention are synthetic molecules that mimic the action of naturally-occurring glycosaminoglycan binding sequences, whether the synthetic molecule is naturally derived, synthetically produced, substantially oligodisaccharide in nature or substantially free of carbohydrate. Such compounds may contain sulfate esters or other negatively charged groups at precise locations in their structures that interact with the basic side chains that characterize the glycan binding site. In this case the analog specifically mimics the binding structure of the natural-sourced sequence. Alternatively, the analog may comprise functional groups that interact with other, different side chains in the glycan binding site, sufficient to allow specific binding interaction of the analog with the glycan binding site, but by means of different contacts. In this case the analog can be said to functionally mimic the protein binding structure of the native "Glyceptor" sequence. Of course, a molecule that is a specific structural mimetic also will be a functional mimetic.

In one embodiment, candidate compounds obtained from nature may be screened as described herein. Alternatively, candidate compounds can be formulated utilizing an approach that includes considerations of size and charge distribution of the "Glyceptor" sequence and glycan binding site it interacts with. Interaction may be achieved by contacts analogous to those made by the endogenous glycan sequence, or by different contacts that produce a functionally equivalent specific interaction at the site. As will be appreciated by those having ordinary skill in the art, by this method analogs having higher or lower binding affinities than that of the endogenous sequence can be obtained. Preferably, and as described herein, a combinatorial "library" containing a group of designed candidates is created, each molecule having a different composition, and the group screened for molecules that bind the ligand of interest above a threshold affinity. A threshold affinity of a candidate "Glyceptor" sequence analog for a preselected glycan-binding protein readily may be determined by means of a standard competition assay, and/or by gel shift assay, as described and exemplified in Examples 3, 7 and 8, below. Preferably, candidates will exhibit binding affinities represented by low dissociation constants, e.g., having Kd values in the range of $10^{-6}$M to $10^{-12}$M, preferably less than $10^{-7}$M or even less than $10^{-8}$M.

A means for designing useful synthetic "Glyceptor" sequence analogs is illustrated in Examples 9 and 10. As described therein, the C-terminal amino acid sequences of a number of glycan-binding chemokines were compared (see FIG. 4), and regions of homology and non-homology were identified. This information, together with an investigation of the known three-dimensional structure for several chemokines (here, IL-8 and PF-4) permits one to identify a physical "map" of the glycan binding site on the effector protein. (See, for example, Baldwin et al. (1991) *PNAS* 88: 502, and Clore et al. (1991) *J. Mol. Biol.* 27: 611.) Characteristically, the glycan binding site is an extended band that stretches across the surface of the protein rather than, for example, defining a pocket, as may occur in enzyme-substrate interactions. Moreover, the glycan binding site typically is defined by a particular distribution of positively charged residues that interact favorably with the anionic charge on the glycosaminoglycan, and also may include other residues that can prevent or limit interaction with particular glycosaminoglycans, either by steric or ionic interference. For example, and as demonstrated by example herein, glycan binding specificity differs between the chemokines PF4 and IL-8. An alignment of the putative glycan binding sites in the C-terminal regions of these proteins identifies the presence of glutamic acid at a position occupied by lysine in PF4 (see FIG. 4.)

Using this type of analysis, a generic structure useful in creating candidate "Glyceptor" sequence analogs can be generated, particularly useful as part of a combinatorial library of candidates. A preferred generic structure is presented in FIG. 5. The generic structure defines an oligomeric structure composed of at least two monomeric units and one or more functional groups pendant therefrom. The position and composition of the pendant functional groups in the generic structure are designed to provide a "library" of useful substituents which can interact with the side chains defining a glycan binding site, whether by making the same contacts as that of the naturally occurring "Glyceptor" sequence, or by making different contacts.

In the figure, each of B1, $B_n$ and B3 represent individual monomeric units that together define the oligomeric backbone. As indicated above, the oligomer may be composed of a minimum of two monomers, or a maximum of eight monomers, all of which are joined by covalent bonds. The backbone has been designed to have an extended, substantially linear structure, although one or more of the monomeric units in fact may be cyclic in structure. Each of the backbone monomeric units B further is defined as having a maximum overall length of no more than that of about 8 carbon-carbon bond lengths, e.g., about 10–12 Å. In a currently preferred embodiment, the overall length of a given monomer unit is in the range of about 4–12 Å. In another preferred embodiment, the overall length of the oligomer does not exceed about 40 Å, and preferably is in the range of about 10–30 Å. Each monomeric unit B independently may be selected from the following useful backbone sequences, all of which have means for polymerization:

(a) ribose or deoxyribose phosphates;
(b) a naturally occurring or synthetic saccharide having polymerization means;
(c) substituted peptides: (—NHCR$_a$HCO—) (preferably, the peptide is not greater than a dipeptide);
(d) N-alkylated glycines (—NCR$_a$H$_2$CO—);
(e) an ester, preferably having a maximum of 6 carbon atoms and polymerization means. Preferred compositions include: (—OCHR$_a$—CO—) or —O—CHR$_a$—CH$_2$—CO—);
(f) aminimides:

(—NR$_a$R$_b$—N—CO—(CR$_c$R$_d$)$_{n'}$—C(OH)R$_e$—CH$_2$—)

or (—NR$_a$R$_b$—N—CO—CR$_c$—NH—CO—(CR$_d$R$_e$)$_{n''}$—C(OH)R$_f$CH$_2$—), where n', n"=0–3;

(g) sulfonamides: (—NH—CHR$_a$—CH$_2$—SO$_2$—); and
(h) ureas: (NR$_a$—CH$_2$—CH$_2$—NH—CO—),
wherein each R$_a$, R$_b$, R$_c$, R$_d$, R$_e$ and R$_f$ represents a linker X as defined herein below having pendant therefrom any of the functional groups R as defined herein below.

As will be appreciated by those skilled in the art, the oligomer thus may have a single chemical character or may be composed of a mixture of chemical structures.

R$_1$–R$_6$; R'$_1$–R'$_6$; R"$_1$–R"$_6$, R$_7$ and R$_8$ each represent possible substituents pendant from the backbone and comprising one or more functional groups for providing the appropriate combination of structural features to interact specifically with a glycan binding site on a protein. Each R independently can be selected from the group consisting of: null entity, —H, hydrocarbons having 1–4 C atoms, $—COR^9$; $—OR^9$; $—HNCOR^9$; $—NR^9R^{10}$; $—NO_2$; halogen, $—CONR^9R^{10}$; $—COOR^9$; $—SO_3R^9$; $—OSO_3R^9$; $COOR^9$; $—NHSO_3R^9$; $—NHC(NH)NH_2$; $—SR^9$; $—C{=}CH_2$;$—C{\equiv}CH$; $OPO_3\ {}_R{}^9R^{10}$; and $—PO_3R^9R^{10}$, wherein $R^9$ and $R^{10}$ independently can be a hydrogen or a hydrocarbon having 1–4 carbon atoms. Accordingly, appropriate ionic interactions with the ligand may be provided by means of sulfates, sulfonates, amines, nitro groups, halogens, hydroxylates, carboxylates, or phosphates.

The pendant substituent functional groups can be attached to the oligomer backbone directly or by means of a linker, X. Accordingly, each X in the formula may define a covalent bond or a linker sequence. Where X defines a linker sequence, the linker sequence is a structure molecule having 1–20 atoms independently selected from the group consisting of C, O, N, S, and P (carbon, oxygen, nitrogen, sulfur and phosphate) atoms in a sequence that may be linear, cyclic or heterocyclic, saturated, unsaturated (including aromatic), aliphatic or hydrophilic. Among useful linkers defined herein are molecules having a phenyl, cyclohexyl, naphthylene, pyridine, indole, imidazole, pyrrole, quinoline, furan, thiophene, oxazole, pyrrolidine, uronic acid, glucosamine, purimidine or purine ring.

It is intended to be understood that attachment of each of the possible R groups to a given linker X (for example R1, R2, R3 to X1) is independent and may occur by attachment of the R groups to the same or different atoms that define the given linker X.

It further is intended to be understood that, while the generic structure provides substituent functional groups by means of the R groups, these are not intended to define the maximum number of substituents pendant from the backbone oligomeric structure. This is represented, for example, by the inclusion of $R_a$, $R_b$, $R_c$ and $R_d$ in the description of allowed backbone monomer units, each $R_a$, $R_b$, $R_c$ and $R_d$ independently defining a linker X as defined herein having pendant therefrom any of the functional groups R as defined herein. Moreover, the backbone monomeric units B themselves may have substituent groups pendant therefrom, which may or may not include one or more of the substituents of the R groups defined herein.

Finally, it will be appreciated that the central backbone unit $B_n$ (and its substituent groups) may be absent or repeated up to 6 times in a given candidate compound. It is further intended each of the internal backbone monomers defined by $B_n$ are independently selected from the group of useful backbone monomer sequences, and that the linker groups $X_5$ and $X_6$, and sustituents $R'_1$–$R'_6$ can vary in form independently of $B_n$.

Candidate compounds constructed following this scheme then can be screened as part of a library, as described in Example 10, preferably using the screening assay exemplified in Example 8, below. Preferably, the dissociation constant of active compounds are between $10^{-6}$M–$10^{-12}$M, more preferably less than $5\times10^{-7}$M, e.g., about $10^{-7}$M, or even less than $10^{-8}$M.

A "Glyceptor" sequence or analog thereof specific for a given ligand conveniently may be isolated by one of several means. For example, a glycan-binding protein of interest is covalently coupled to a support by any of a number of methods well known to those skilled in the art. This produces an affinity binding material which may then be used to select a GAG sequence to which the ligand will specifically bind through its natural GAG binding domain. (See Example 1, below.) Alternatively, the technique of affinity coelectrophoresis may be used to advantage to select "Glyceptor" sequences and assess binding affinity (see Example 2, below.)

Where the "Glyceptor" sequence or analog to be isolated is a natural-sourced glycosaminoglycan sequence, the source for natural, specific GAG oligosaccharide may depend to some degree on the glycan-binding protein of interest. For example, liver and skin will be appropriate sources for chemokines that are involved in inflammatory processes. Alternatively, for a chemokine that participates in immune cell trafficking, lymph nodes, intestinal mucosa, or thymus may be chosen as the GAG source. For chemokines such as MCP-1, a preferred source of GAG material may be the synovial tissue removed from a joint afflicted with rheumatoid arthritis. Methods are well established for the preparation of these materials. Enzyme digestion typically will be used to fragment the GAG chains into oligosaccharides of defined size. Where the ligand is a growth factor, useful sources of candidate GAG sequences include tumors and placenta. Where the ligand is an enzyme or other protein involved in lipid metabolism a useful GAG source is liver.

Provided below are numerous examples disclosing how to identify useful oligodisaccharide sequences having specificity for a ligand of interest (Examples 1–3), how to generate various "Glyceptor" sequence and ligand analogs (Examples 3, 4, 7, 9–12) and how to test for their effectiveness in vitro and in vivo (Examples 2, 4, 6–8, 12).

While the Examples provided below illustrate various methods and compositions of the invention, and most of them are "Glyceptor" sequence antagonists, it will be appreciated by those skilled in the art that other types of analogs, including agonists, may be obtained and utilized using the teachings of the specification, and accordingly are contemplated herein.

The "Glyceptor" sequence antagonist or ligand antagonist for use as a therapeutic agent prepared as described herein may be provided to an individual by any suitable means, preferably directly or systemically, e.g., parenterally, preferably in combination with a pharmaceutically acceptable carrier. As used herein, "a physiologically acceptable carrier" includes any and all solvents, dispersion media, antibacterial and antifungal agents that are non-toxic to humans, and the like. Particularly contemplated are pharmaceutically acceptable salts, which may be base salts, alkali metal salts, and alkaline metal salts. The use of such media and agents as pharmaceutically active substances are well known in the art.

Where the therapeutic agent is to be provided directly (e.g., locally, as by injection, to a desired tissue site), or parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, for example, the therapeutic agent preferably comprises part of an aqueous solution. The solution is physiologically acceptable so that in addition to delivery of the desired therapeutic agent to the patient, the solution does not otherwise adversely affect the patient's electrolyte and volume balance. The aqueous medium for the therapeutic agent thus may comprise normal physiologic saline (0.9% NaCl, 0.15M), pH 7–7.4.

Useful solutions for oral or parenteral administration may be prepared by any of the methods well known in the pharmaceutical art, described, for example, in *Remington's Pharmaceutical Sciences*, (Gennaro, A., ed.), Mack Pub., 1990. Formulations may include, for example, useful excipients to control the release of the therapeutic agent in vivo. The therapeutic agents also provided herein may be administered alone or in combination with other molecules known to have a beneficial effect in, for example, modulating the inflammatory response, and/or which may enhance targeting of the agent to a desired tissue or cell surface. Other useful cofactors may include symptom-alleviating cofactors, including antiseptics, antibiotics, antiviral and antifungal agents and analgesics and anesthetics.

The compounds provided herein can be formulated into pharmaceutical compositions by admixture with pharmaceutically acceptable nontoxic excipients and carriers. As noted above, such compositions may be prepared for parenteral administration, particularly in the form of liquid solutions or suspensions; for direct administration, in the form of powders, nasal drops or aerosols.

The compositions can be formulated for parenteral or oral administration to humans or other mammals in therapeutically effective amounts, e.g., amounts which provide appropriate concentrations of the agent to target tissue for a time sufficient to inhibit the desired ligand-"Glyceptor" sequence interaction of interest, as described above.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of tissue loss or defect, the overall health status of the particular patient, the relative biological efficacy of the compound selected, the formulation of the compound, the presence and types of excipients in the formulation, and the route of administration. In general terms, the compounds of this invention may be provided in an aqueous physiological buffer solution containing about 0.001 to 10% w/v compound for parenteral administration. Typical dose ranges are from about 10 ng/kg to about 1 g/kg of body weight per day; a preferred dose range is from about 0.1 µg/kg to 100 mg/kg of body weight. It will be appreciated by those having ordinary skill in the art that analogs having higher binding affinities typically will require lower total administration concentrations than those having comparatively lower binding affinities.

ABBREVIATIONS

Throughout the present specification the following abbreviations and terms are used:

"Glyceptor" sequence—protein-specific glycosaminoglycan sequence; HS—heparan sulfate; HSPG—heparan sulfate proteoglycan; GF—growth factor; dp—degree of polymerization (e.g. for a disaccharide, dp=2, etc); GlcA—glucuronic acid; IdoA—iduronic acid; IdoA(2S)—iduronic acid 2-sulfate; GlcNAc—N—acetyl glucosamine; GlcNSO$_3$—N-sulfated glucosamine; GlcNSO$_3$ (6S)—N-sulfated glucosamine 6-sulfate; GlcA(2S)—glucuronic acid 2-sulfate; PBS, phosphate-buffered saline.

Chemokines

α Subfamily

Platelet factor 4 (PF-4)

Interleukin 8 (IL-8)

Platelet basic protein (PBP)

Connective tissue activating peptide III (CTAP III)

β Thromboglobulin

Neutrophil activating peptide 2 (NAP-2)

Melanocyte growth stimulating activity (MGSA) also known as GRO α

GRO β

GRO γ

Epithelial derived neutrophil activating factor (ENA-78)

γIP10

β Subfamily

Monocyte chemotactic peptide-1 (MCP-1) (also known as monocytechemotactic and activating factor, (MCAF);

Monocyte chemotactic peptide-2 (MCP-2);

Monocyte chemotactic peptide-3 (MCP-3);

RANTES, also known as SIS (small, inducible, secreted);

Macrophage inflammatory peptide 1α, also known as LD78;

Macrophage inflammatory peptide 1β, also known as ACT-2; and

I309

Growth factors known to bind heparin

Basic fibroblast growth factor (bFGF)

Acidic fibroblast growth factor (aFGF)

Heparin binding epithelial growth factor (HB-EGF)

Platelet derived factor (PDGF)

Hepatic growth factor (HGF)

Vascular endothelial growth factor (VEGF) also known as vascular permeability factor (VPF)

IL3

Granulocyte macrophage stimulating factor (GMSF)

Other members of the fibroblast growth factor family include: int-2, hst/KFGF, FGF-5, and KGF Enzymes Lipoprotein lipase (LPL)

Hepatic triglyceride lipase (HTGL)

Extracellular superoxide dismutase (ECSOD)

Antithrombin III (AT III)

Lipid transport proteins

Apolipoprotein B-100

Apolipoprotein E

EXAMPLES

Example 1
Identification of Specific "Glyceptor" Sequence Sequence That Binds Growth Factor of Interest Useful "Glyceptor" sequences may be identified following the method of Habuchi et al., described in EP application EP 0509517A2, public Oct. 21, 1992, or following the method of Turnbull et al. (1992) *J. Biol. Chem.* 207:10337–10341. As described therein, the ligand of interest, e.g. a growth factor, is immobilized on a suitable surface, or carrier, such as a chromatography matrix, to form an affinity column. Useful carriers include agarose gel and the like, preferably Sephadex (available from Pharmacia), Biogel (available from Bio-Rad Laboratories), Sepharose (available from Pharmacia) and the like. Other useful matrices include electrophoresis matrices, as described, for example, in Example 3, below. The glycosaminoglycan to be tested for candidate "Glyceptor" sequences first is radioactively labeled using, for example, tritium, so that the candidate oligodisaccharide fractions can be followed. The glycosaminoglycan then is digested with one or more suitable enzymes (e.g., pronase) and the digested fractions then run over the bound ligand to be tested for binding affinity. Specificity of binding then is determined by preferential elution with, for example, an eluant of increasing ionic strength. (See FIG. 3B) The saccharide sequence of oligodisaccharides having the desired binding affinity then can be determined using discrete enzymes that recognize specific saccharide and/or disaccharide units (e.g., heparinase and heparitinase, which distinguish between disaccharides containing 2-0-sulfated iduronate and glucuronic acid.) The role of N-sulfate groups also can be confirmed by assessing binding on affinity column of oligodisaccharides following deamination with nitrous acid and/or following desulfation and re-N-acetylation of candidate oligodisaccharide, using standard procedures well known in the art and described by Habuchi et al. and Turnbull et al.

In the example below, a "Glyceptor" sequence which has specificity for basic fibroblast growth factor (FGF) is described, essentially as described by Habuchi et al. As will be appreciated by those having ordinary skill in the art, the procedure exemplified below readily can be modified for any effector molecule of interest.

1.1 Preparation of GF-Sepharose

200 μg of a given GF is dissolved in 0.5 ml of a coupling buffer (0.1M $NaHCO_3$ containing 0.4M NaCl, pH 8.3). To the resulting solution is added 200 μg of heparan sulfate previously treated with acetic anhydride (prepared, e.g., from swine aortas, using any one of a number of standard procedures well known in the art). The mixture is allowed to stand at room temperature for 10 minutes.

0.5 ml Sepharose (available from Pharmacia), previously activated with cyanogen bromide (CNBr), is suspended in the same volume of the coupling buffer, and the GF solution prepared above is added thereto. The resulting mixture is gently shaken overnight at 4° C.

The gel thus obtained is washed thoroughly with the coupling buffer and suspended in 900 μl of Tris-HCl buffer (0.1M, pH 8.0), and the resulting suspension gently shaken overnight at 4° C. to prepare GF-Sepharose.

1.2 Preparation of a standard heparan sulfate elution curve using bFGF-Sepharose Heparan sulfate is treated with [$^3$H] $NaBH_4$ to label (tritiate) the reducing end of heparan sulfate using standard tritium labeling techniques well known and described in the art. The labeled sulfate then is subjected to chromatography using a column packed with the GF-Sepharose, and the tritium ($^3$H) present in the eluate monitored by standard means to prepare a standard elution curve.

1.3 Fractionation of heparan sulfate having high affinity for GF

Buffer A is prepared by dissolving chondroitin sulfate (shark origin, available from Seikagaku Corporation) to a final concentration of 0.02% (wt/vol) in 0.1M phosphate buffer containing 0.9 mM of $CaCl_2$ and 0.48 mM of $MgCl_2$ (PBS pH 7.2).

100 μg of heparan sulfate (e.g., swine aorta-derived) is dissolved in three volumes of buffer A, applied to a GF-Sepharose column and gently shaken at 4° C. for 2 hours.

The column is washed with buffer A to remove heparan sulfate which does not bind to the affinity gel and then subjected to a linear concentration gradient elution with PBS/3M NaCl. After digestion with chonodroitinase, the hexuronic acid value of chondroitinase-resistant substances in the eluate is measured according to an elution curve which has been prepared by monitoring $^3$H radiation of a standard sample thereby preparing an elution curve, and fractionating a heparan sulfate portion having a high affinity for GF.

1.4 Preparation of oligosaccharide having affinity for GF

The thus obtained heparan sulfate fraction having a high affinity for GF can be treated in the following manner to prepare a mixture of oligosaccharides.

A 50 Milli-unit portion of Heparitinase 1 (EC 4.2.2.8, available from Seikagaku Corporation) 25 μmol of Tris-HCl buffer (pH 7.2), 0.5 μmol of $CaCl_2$ and 50 μg of bovine serum albumin and made into a 500 μl solution. To this is added 5 mg of the heparan sulfate fraction having a high affinity for GF and the resulting mixture incubated at 37° C. for 60 minutes to prepare a mixture of oligodisaccharides. The reaction is terminated by heating at 100° C. for 2 minutes.

A 50 μg portion of the thus obtained oligodisaccharide mixture is dissolved in 300 μl of the aforementioned buffer A and the solution applied to a GF-Sepharose column which has been calibrated in advance with a standard sample. After shaking at 4° C. for 2 hours, oligodisaccharide portions which do not bind to the carrier are removed by washing with 5 ml of the buffer A and elution is carried out with PBS buffer containing 3M NaCl.

1.5 Purification of Oligosaccharide having affinity for GF.

The thus obtained oligodisaccharide fraction is further purified by applying it to a column (1.2×120 cm) packed with Sephadex G-50 (available from Pharmacia) and eluting with 0.5M NaCl.

An elution curve is prepared in advance by using a $^3$H-labeled standard sample. Following this method a broad elution pattern is obtained with a peak which corresponds to hexadeca- to octadecasaccharides.

Example 2A

Demonstration of specificity of "Glyceptor" sequence binding by a chemokine using affinity coelectrophoresis The following examples describe a method for identifying oligodisaccharide sequences having specificity for a chemokine, in this example IL-8. Those having ordinary skill in the art will appreciate that this method may be applied to the identification of oligodisaccharides which bind other chemokines or other ligands, without undue experimentation.

Commercial heparin (porcine mucosa, Sigma Biochemical) is radioactively labeled by first incorporating tyramine at the reducing end of the chains and then introducing radioactive iodine using the chloramine T reaction, a procedure well known in the art. The heparin is size fractionated on a Sephadex G-100 column (Pharmacia) and the last 10% of the heparin to elute is selected and utilized for the labeling. The labeled low molecular weight heparin is then bound to varying concentrations of IL-8 under equilibrium conditions using the technique of affinity coelectrophoresis, as described by Lee and Lander, Proc. Nat. Acad. Sci., U.S.A. (1991) 88, 2768–2772. Briefly, a horizontal 1% agarose gel is poured, using low melting point agarose, that contains nine rectangular wells of equal dimensions (about 3×10 mm). The buffer used comprises 125 mM sodium acetate, 50 mM MOPSO, pH 7.0, 0.5% 3-[3-cholamidopropyl) dimethylammonio]-1-propanesulfonate (CHAPS) may be used in the buffer to prevent adventitious binding of protein to vessel walls. The wells in the horizontal gel are subsequently filled with a requisite amount of 1% agarose which contains varying concentrations of IL-8 ranging from about 80 nM up to about 80 µM. The IL-8 may be produced by recombinant means as is well known in the art or may alternatively be produced as a synthetic peptide. The radioactive heparin is placed into a long well which lies above the discontinuous gradient of IL-8 at a final concentration of 4 ng/ml, a concentration well below that of the lowest concentration of IL-8. The gel is subjected to electrophoresis at 100 volts for one hour in the same buffer as used for the gel with the electrodes placed in such a way as to cause the negatively charged heparin to migrate through the wells containing the IL-8. This brings the heparin chains into contact with the IL-8 molecules and, depending upon the affinity of binding, complex formation may or may not occur.

Following electrophoresis, the gel is dried and subjected to autoradiography to visualize the pattern formed by the heparin. As described in the above-cited Lee and Lander reference, formation of a complex between the protein molecules and the heparin chains leads to a significant retardation in migration. From this the binding affinity of the protein, in this case IL-8, for the heparin may be accurately measured. In the specific instance of antithrombin III (AT III), two affinities can be measured as described in the cited reference. The two detected affinities arises from the existence of two types of heparin chain present in the heparin fraction used; one which contains sequence having a substantially high affinity for a AT III binding site, and another which does not contain the high affinity site but rather contains a sequence wherein binding is primarily by non-specific interactions.

When IL-8 is fractionated as described, a similar high affinity and a low affinity binding profile is apparent, indicating the existence of a specific, IL-8 binding fraction within the commercial heparin preparation.

Using the procedure described above and in U.S. Pat. No. 5,116,483, the binding affinity of four chemokines: PF4, IL-8, NAP2 and GROα for radioiodinated (approx. $10^4$ cpm/sample) low molecular weight heparin, prepared as described above, was measured. The results are represented in FIG. 6, wherein the concentrations referenced for each lane in the figure indicate the concentration of chemokine present in that lane.

The series of peaks, increasing from right to left, represent the progressive retardation of heparin mobility in the presence of increasing amounts of each chemokine. The valleys between each peak are due to the presence of chemokine-free agarose between each lane, and serve to help align the peaks with the lanes. From such electrophoetograms, the apparent dissociation constant can be estimated from the protein concentration at which heparin is half-maximally retarded (See, for example, U.S. Pat. No. 5,116,483). The estimated dissociation constants are: Groα, $2.5 \times 10^{-7}$M; PF-4, $2.7 \times 10^{-8}$M; IL-8, $9.1 \times 10^{-7}$M; and NAP2, $2.5 \times 10^{-7}$M.

Example 2B

Confirmation that the isolated high affinity fraction of heparin is specific for IL-8 binding.

Figure 3A:
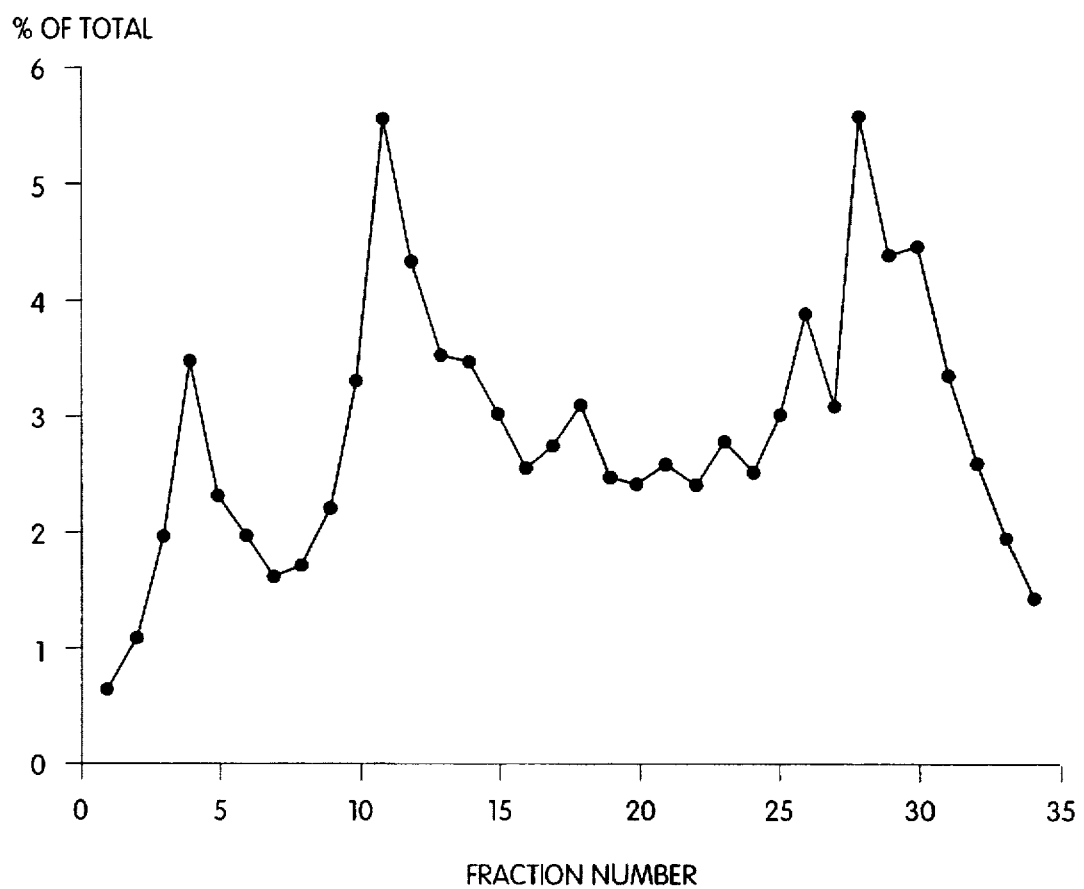
FIG. 3A is a representative plot of the adioactivity measured in 0.3 cm gel slices (fractions) from an affinity coelectrophoresis analytical gel. Peaks represent distinct, separated bound complexes.

An agarose gel is cast as above but with a large central well (about 4×7 cm). This is filled with a 1% agarose solution containing 1 µM IL-8, a concentration which was shown to effectively separate the low and high affinity fractions of heparin. Conditions of electrophoresis are as before except that the gel is run for 1½ hour at 100 volts. Following electrophoresis, the gel is sliced into 3 mm pieces and the radioactivity of each piece is determined (see, for example, FIG. 3A). This reveals the expected pattern of a high affinity and a low affinity fraction as well as a peak fraction of intermediate affinity. The peak fractions are pooled and melted at 65° and sufficient urea is added to make a final concentration of 6M. This prevents the agarose from regelling.

These fractions are then rerun under analytical conditions as described above. This confirms that the commercial heparin contains a minor fraction which has a reproducible dissociation constant of about 100 nM ($10^{-7}$M) or less for binding IL-8. The low affinity fraction binds IL-8 with a dissociation constant of greater than 1 µM (1000 nM). The high affinity fraction of heparin thus shows an affinity for IL-8 which is characteristic of a specific interaction such as exists between AT III and the defined AT III binding site. The fraction of heparin showing high affinity for IL-8 is not however identical to the fraction of heparin showing high affinity for AT III although some overlap may occur. This suggests the existence of heparin chains which bear both the specific AT III binding site and the specific IL-8 binding site.

The heparin fractions which are separated by electrophoresis on IL-8 also were evaluated for binding to other chemokines, e.g. PF4, NAP-2, and GROα, using the same techniques as described above. The results are presented in FIG. 7. PF4 and NAP-2 are found either to not differentiate or to differentiate poorly between the high affinity and low affinity fractions. Thus, PF4 and NAP-2 do not recognize the same "Glyceptor" sequence as IL-8. By contrast, GROα binds with high affinity to the "Glyceptor" sequence recognized by IL-8, and much more weakly, i.e. 20–25 fold less, to the low affinity species obtained by fractionation on IL-8, suggesting that GROα may bind to the same or a similar glycan structure as does IL-8.

Example 2C

Preparation of a heparin fraction enriched in an IL-8 binding site.

Two methods may be used to advantage for the preparation of specific "Glyceptor" sequences for further studies. Affinity coelectrophoresis, essentially as described above and herein below may be utilized in a preparative fashion to produce sufficient quantities of material for further studies. Alternatively, if larger quantities are required, affinity chromatography may be used.

2C.1 Preparation by affinity coelectrophoresis

In the former case, a horizontal 1% agarose gel of approximate dimensions 10×15×0.5 cm is poured using the same buffer as described above and low gelling point agarose (FMC Corporation). Instead of incorporating 9 wells into the gel as before, however, a large central well is introduced of about 4×6×0.5 cm in addition to the long well of about 0.2 cm×6 cm×0.5 cm which will contain the heparin sample. After the gel has cooled, 7.5. ml of IL-8 at 2× the appropriate concentration to effectively separate the high affinity from the low affinity heparin chains (typically 2–5 µM) and heated to 37°. This is then introduced into the central well of the precast gel and allowed to set. This constitutes the preparative ACE gel which can be used to provide sufficient quantities of specific "Glyceptor" sequence for use in "Glyceptor" sequence screening assays and for "Glyceptor" sequence characterization studies.

In order to use the preparative ACE gel to provide purified "Glyceptor" sequence, an amount of radioactively labeled heparin is loaded into the remaining well and electrophoresed at 100 volts for about 1 hour using the MOPSO-based buffer. This results in the heparin migrating through the region of the gel containing IL-8 which causes the high affinity heparin to be separated from the lower affinity binding species. The gel is then sliced into fractions of 0.3 cm each and the fractions counted. This results in the production of defined peaks of radioactivity which correspond to the heparin species of varying affinity (see FIG. 3A.) The highest affinity, i.e. most retarded species, is defined as the specific "Glyceptor" sequence.

The "Glyceptor" sequence preparation can be used by melting the agarose gel and adding solid urea to a final concentration of 6M which will prevent the agarose from regaling. Alternatively, the melted agarose may be diluted into a larger quantity of buffer (for example 1:20) which may then be used directly in "Glyceptor" sequence screening assays. If it is desired to concentrate the "Glyceptor" sequence, this may be conveniently done by, for example, binding a polyanionic "Glyceptor" sequence to an appropriate anion exchange matrix, for example, DEAE-cellulose, and subsequently eluting the bound "Glyceptor" sequence with 2M NaCl.

2C.2 Preparation by affinity chromatography

Figure 3B:
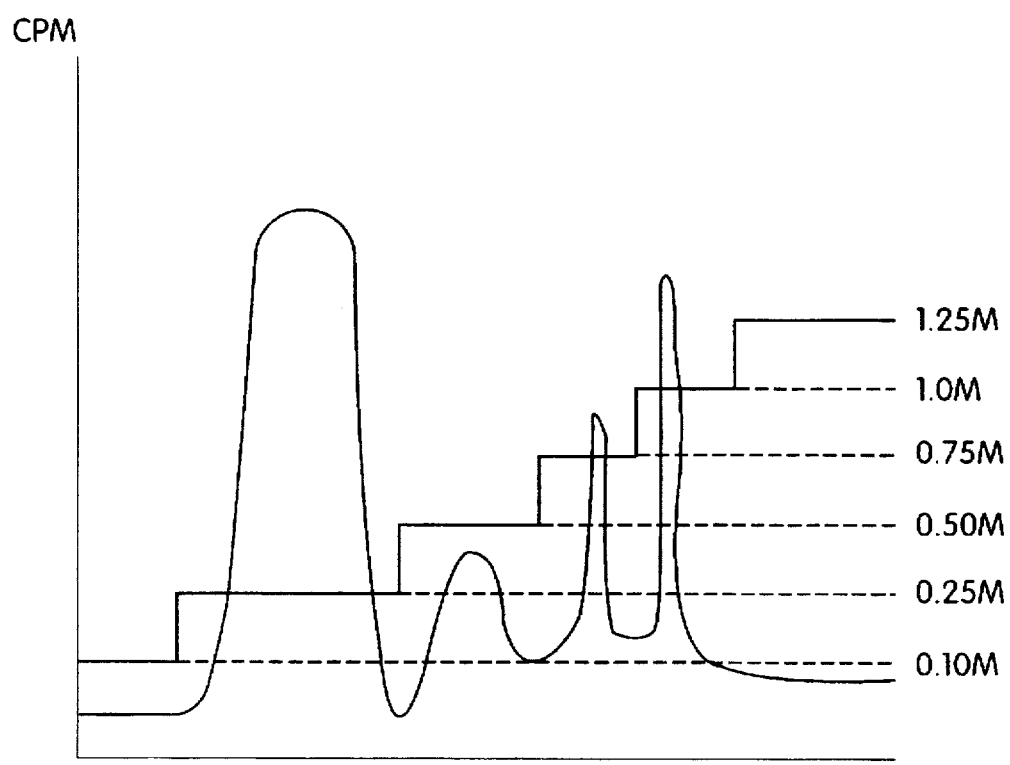
FIG. 3B is a representative plot of an elution profile obtained by binding radioactively labeled oligodisaccharide fragments derived from glycosaminoglycan chains to a immobilized ligand matrix, eluting fractions using a step gradient of increasing ionic strength. The oligodisaccharide sequences eluting at 0.5M bind with moderate affinity to the ligand. Preferred, higher selectively sequences will elute at higher ionic strength eluent, most preferably above about 0.7M.

If larger quantities of "Glyceptor" sequences are required, for example, for structural characterization, affinity chromatography may be the preferred preparative method. In this case, IL-8 is immobilized on a solid support such as acrylamide or agarose beads using standard techniques. The efficiency of the immobilization process can be improved by including heparin along with the IL-8 during the immobilization step. The affinity column is washed and, if heparin was prebound, is stripped with 2M NaCl in an appropriate buffer. The washed column then is loaded with heparin and is eluted with a gradient of NaCl ranging from about 0.1M to about 1.5M salt in an appropriate buffer such as 0.05M phosphate, pH 6.8. It also may be desirable to include 1 mM EDTA to chelate divalent cations. The heparin fractions which elute at the lower concentrations of salt are discarded and the fraction eluting at the highest concentration is collected and dialyzed. This fraction typically may elute a concentration of 0.5M or higher NaCl and represents the fraction of heparin which contains the specific IL-8 binding site (see, for example, FIG. 3B, illustrating such an elution profile.)

Recognition of this "Glyceptor" sequence binding "domain" allows a person having ordinary skill in the art to create "Glyceptor" sequence analogs specific for a glycan-binding protein of interest with relative ease. For example, and as described herein below, synthetic organic mimetics can be designed. Alternatively, using standard procedures, antibodies can be raised that recognize one or more epitopes on the glycan binding site.

Alternatively, a glycan-binding protein analog, particularly an antagonist or "ligand decoy" may be created using standard recombinant DNA and protein chemistry technology. In one embodiment, the glycan-binding protein is an effector protein and the mutein is designed to substantially interfere or prevent receptor binding without affecting "Glyceptor" sequence binding. (See below.)

Example 3

Preparation of a heparan sulfate fraction which is enriched in a specific IL-8 binding site.

The affinity column employed in the previous example may be used in the same fashion to isolate an HS fraction enriched in a specific IL-8 binding site. Heparan sulfate (bovine mucosa, Sigma Biochemical, Co., Cincinnati) is loaded into the column and eluted with a salt gradient of 0.1M to 1.5M NaCl in a buffer containing 1 mM EDTA. As with heparin, a tight binding fraction is identified which elutes at a salt concentration greater than 0.5M. With some preparations of heparin the salt concentration required for elution of the tight binding fraction may vary somewhat and may exceed that required for elution of the high affinity heparin fraction. This indicates that some microheterogeneity may occur in the specific "Glyceptor" sequence which binds IL-8 and that some slight variation in binding affinity may occur as a result.

Example 4

Determination of a specific glycosaminoglycan composition

The specific composition of a particular glycan sequence may be determined following the methods of Turnbull et al., (1992) *J. Biol. Chem.* 267:10337–10341 and Habuchi et al., (1992) *J.Biochem.* 285:805–813, the disclosures of which are incorporated herein by reference. Briefly, a particular glycosaminoglycan fraction is isolated or otherwise prepared as described in Example 1, above. The composition of the oligodisaccharide then is determined by exhaustive digestion with a variety of oligodisaccharide-specific enzymes that discriminate between the four classes that define oligodisaccharides. Useful enzymes include heparitinase I, heparitinase II and heparinase. The digested glycans then separated by standard means, e.g., HPLC, using a polyamine-bound silica PAMN column. Specific disaccharides then are eluted separately using an elution gradient. Separated disaccharides then can be degraded by deamination with nitrous acid at pH 1.5, and the products reduced by addition of [$^3$H]NaBH, following the method of Shively et al. (1976) *Biochem.* 15: 3932–3942. Separation by molecular weight, together with an analysis of the enzymatic digestion results, provide one with a profile of the glycan saccharide composition. Using this methodology, Habuchi et al. determined that endogenous heparin has within its sequence a binding site specific for aFGF and whose composition is [IdoA(2SO$_4$)GlcNSO$_3$ (6SO$_4$)]$_3$.

Example 5

Demonstration of a chemokine-specific anti-inflammatory effect in an organism using a specific "Glyceptor" binding sequence isolated from heparin.

The following example describes a general method for demonstrating the antiinflammatory effect of a "Glyceptor" sequence antagonist, and a general method for administering a therapeutic agent based on procedures for treatments to alleviate or correct chronic inflammation and other autoimmune disorders. In this example, heparin provided the source for the "Glyceptor" sequence antagonist tested on IL-8 action. However, as will be appreciated by those skilled in the art, the assay may be modified without undue experimentation to test other antagonists, and other effector proteins.

Heparin chains containing the specific IL-8 binding sequence (high affinity heparin binding sequence or HAHBS) obtained as described in Example 3 are injected intravenously into a mouse to produce an inhibitory effect on IL-8 mediated inflammation. Typically about 50–100 μl of a sample of 1–2 μg of HAHBS suspended in phosphate buffered saline (PBS) or alternatively an equivalent amount of PBS alone is injected into the tail vein of a mouse at the same time that 1 μg of IL-8 is introduced into the peritoneal cavity. After 3 hours the peritoneal cavity is lavaged and the infiltrated cells are counted. The animals which receive only the excipient show a profound and selective influx of polymorphonuclear leukocytes into the peritoneal cavity while the animals which were injected with HAHBS sown a dramatic reduction in the number of PMN's present relative to the saline treated animals. The reduction is typically greater than 60%. This demonstrates that the heparin chains which contain the high affinity binding sequence for IL-8 are able to effectively displace the IL-8 molecules from the specific "Glyceptor" sequence sites on the endothelial surface. As a result, the PMN leukocytes are not able to be efficiently activated and are prevented from leaving the bloodstream.

Example 6

Demonstration of a chemokine-specific anti-inflammatory effect in an organism using a specific "Glyceptor" binding sequence from heparan sulfate.

Heparan sulfate chains containing the specific IL-8 binding sequence (high affinity heparan sulfate binding sequence or HAHSBS) obtained as described in Example 4 are injected intravenously into a mount to produce an inhibition of the response to IL-8. Typically about 50–100 μl of a sample of 1–2 μg of HAHSBS suspended in phosphate buffered saline (PBS) or alternatively an equivalent amount of excipient alone is injected into the tail vein of a mouse at the same time that 1 μg of IL-8 is introduced into the peritoneal cavity. After 3 hours the peritoneal cavity is lavaged and the infiltrated cells are counted. As before, the animals which receive only the excipient show a profit influx of polymorphonuclear leukocytes into the peritoneal cavity while the animals which were injected with the HAHSBS show a dramatic reduction in the number of PMN's present relative to the control. The reduction is typically greater than 50–70%. This demonstrates that the heparin chains which contain the high affinity binding sequence for IL-8 are able to effectively displace the IL-8 molecules from the specific "Glyceptor" sequence sites on the endothelial surface. As a result, the PMN leukocytes are not able to be efficiently activated and are prevented from leaving the bloodstream.

Example 7

Demonstration of an anti-inflammatory effect in an organism using a agent which selectively displaces chemokines by binding tightly to a "Glyceptor" sequence on the endothelium.

This experiment is conducted in a similar way to those described in the preceding examples, except that protamine chloride is injected intravenously in place of the "Glyceptor" sequence chains. Typically a dose of 100–250 mg is suspended in PBS and injected into the tail vein of the mice. IL-8 is again injected into the peritoneal cavity. As previously, a significant inhibition of neutrophil influx is seen.

In the preceding examples the selected HAHBS and HAHSBS provide an anti-inflammatory effect through their ability to specifically bind to the "Glyceptor" sequence binding site of the IL-8 molecule which then displaces the IL-8 from the endothelial surface into the blood where it is carried away from the site of inflammation. Although protamine chloride is not specific in its ability to bind to glycosaminoglycan chains but rather binds randomly to all "Glyceptor" sequences, it has the ability to displace bound IL-8 molecules by binding to the glycosaminoglycan chain rather than the protein with the same ultimate effect. While the lack of specificity of protamine makes it a generally toxic agent, this nonetheless demonstrates that an effective inhibitory agent may be directed toward the "Glyceptor" sequences as well as toward the protein ligand. The toxicity of protamine precludes its use as an inflammatory agent but the demonstration of specific sequences in glycosaminoglycan chains for binding chemokines and other factors provides the basis for selection of agents which provide an anti-inflammatory effect by binding in a specific fashion to a "Glyceptor" sequence and selectively washing off inflammatory molecules which are presented. Information provided herein combined with selection and screening techniques well known to those practiced in the art can be used to identify such agents.

Example 8

Isolation of a ligand-"Glyceptor" sequence complex; Demonstration of ligand-"Glyceptor" sequence binding inhibition with synthetic "Glyceptor" sequence antagonists Purified "Glyceptor" sequences are used herein below in conjunction with a cognate chemokine or other glycan-binding effector protein to create a binding assay to screen for effective inhibitors, e.g., candidate "Glyceptor" sequence antagonists. The selected candidate antagonists are expected to be useful as therapeutic agents in vivo because of their ability to displace glycan-binding effector proteins from their "Glyceptor" sequences. A competition assay representing a useful screening assay is described below and results are presented showing binding specificity of various synthetic organic molecules with representative chemokines and growth factors.

Example 8A

"Glyceptor" sequences are purified as described above. Chemokines may be purchased from commercial suppliers or may be made by techniques well known to those skilled in the art. The binding assay typically is conducted by suspending an appropriate amount of radiolabeled "Glyceptor" sequence, for example 1000–2000 dpm, in 0.5 ml of an appropriate buffer, for example, phosphate buffered saline. To this solution then is added an additional 0.5 ml of buffer containing 0.1% carrier protein (e.g. bovine serum albumin or ovalbumin) plus an amount of the chemokine of interest sufficient to result in the binding of >90% of the "Glyceptor" sequence present. The amount of chemokine to be added may be determined from the binding constant of the chemokine for the "Glyceptor" sequence. For example, in the case of IL-8, a protein concentration of 1 µM or more will result in binding of more than 90% of the "Glyceptor" sequence present in the assay. Binding is allowed to occur for about 30 minutes to 2 hours and the assay mixture then is filtered through a nitrocellulose membrane using a vacuum assist, so that the chemokine is captured on the nitrocellulose. If the radioactive "Glyceptor" sequence is complexed with the chemokine it also remains associated with the nitrocellulose filter, if it is not complexed, the "Glyceptor" sequence passes through the membrane unbound. The quantity of the "Glyceptor" sequence bound to the chemokine then can be conveniently determined by counting the radioactivity associated with the filter.

In order to select the most effective "Glyceptor" sequence antagonists from among a library of compounds, the assay may be utilized as follows as a screening assay. Each compound to be tested within the library is suspended in an appropriate buffer, e.g. PBS, to a final concentration of about 100 µM. Twenty to fifty µl of each compound solution is added to the 0.5 ml of buffer containing radiolabeled "Glyceptor" sequence prior to the addition of the chemokine solution. 0.5 ml of the chemokine solution then is added and incubation is carried out as above. The final concentration of the compound to be tested is thus 2–5 µM in the final assay mixture. The concentration of the compound to be tested may be raised or lowered as needed to increase or decrease the stringency of the screening assay. For example, to increase the stringency of the assay, lower concentrations should be used; to decrease the stringency, higher concentrations may be used.

Figure 8:
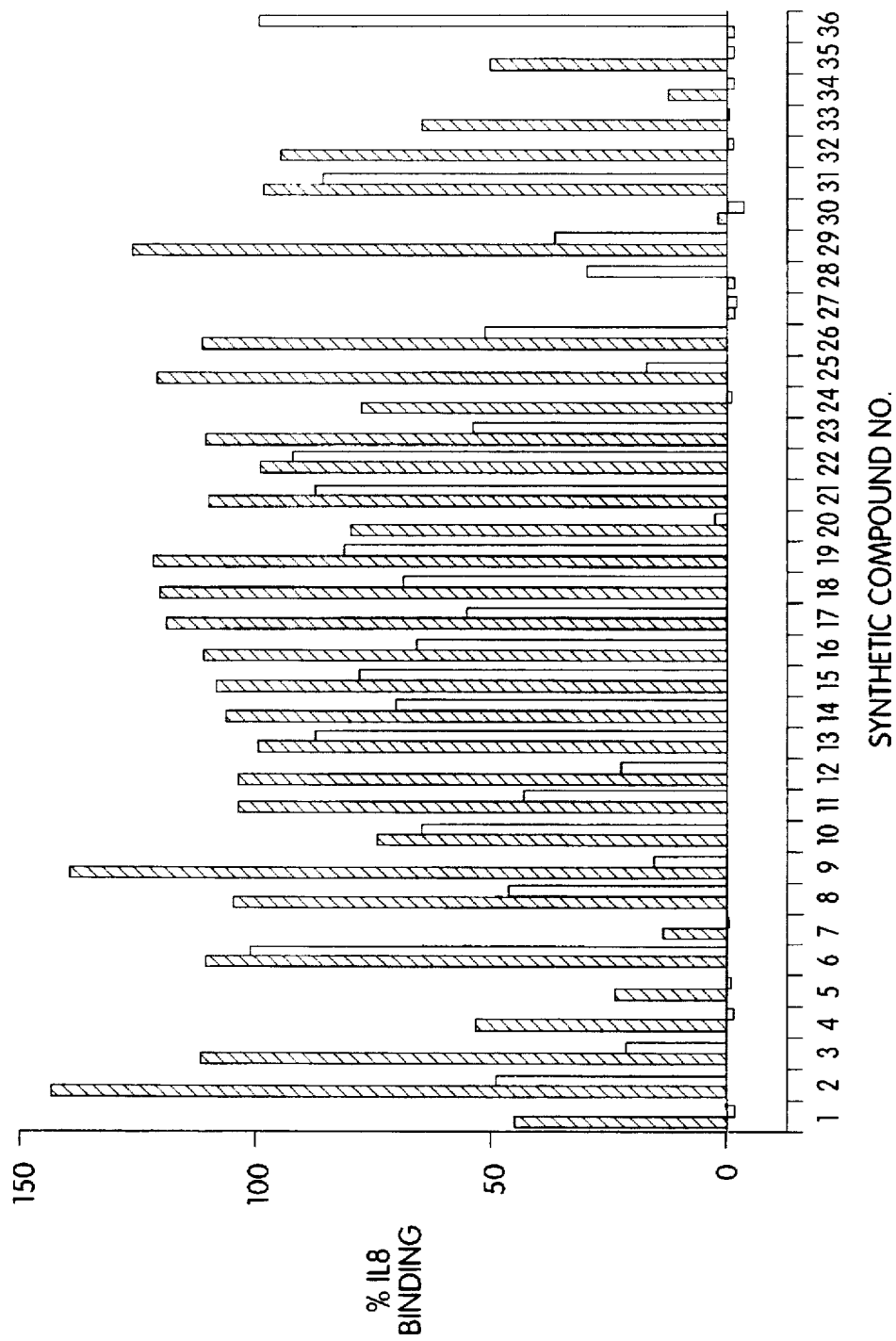
FIG. 8 compares the inhibitory effect of 36 different polysulfonated naphthylurea compounds on IL-8- "Glyceptor" sequence binding (closed bars) and GROα- "Glyceptor" sequence binding (open bars)
Figure 9:
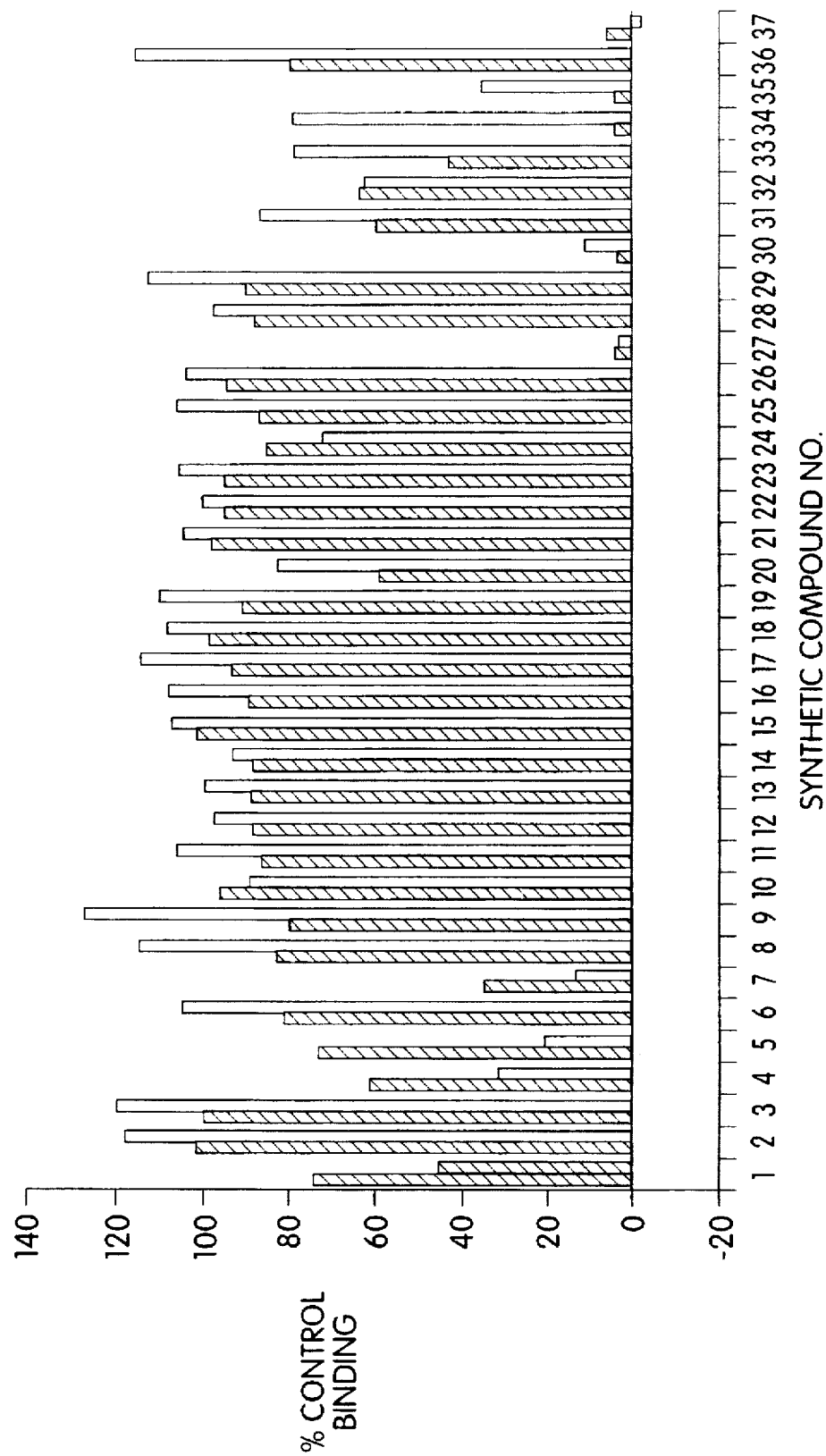
FIG. 9 compares the inhibitory effect of 36 different polysulfonated naphthylurea compounds on FGF- "Glyceptor" sequence binding (closed bars) and IL8- "Glyceptor" sequence binding (open bars)

As an example, a collection of 36 different synthetic polysulfonated naphthylureas ("Syn #" 1–36) having certain structural features characteristic of heparin sulfate, were screened for "Glyceptor" sequence antagonist activity using an assay as described above. The results shown in FIGS. 8 and 9. FIG. 8 compares the effectiveness of the various compounds in blocking "Glyceptor" sequence binding to two different chemokines: IL-8-"Glyceptor" sequence binding relative to GROα-"Glyceptor" sequence binding. FIG. 9 compares the effectiveness of the various compounds in blocking "Glyceptor" sequence binding to a chemokine or a growth factor: IL-8-"Glyceptor" sequence binding relative to FGF-"Glyceptor" sequence binding. As can be seen from the figure, certain compounds effectively inhibited the binding of both chemokines to their "Glyceptor" sequences (e.g., Syn #27, Syn #30). Other compounds preferentially inhibited only one of the chemokines (e.g., Syn #4, Syn #12.) The data demonstrates the ability of the "Glyceptor" sequence screening assay to identify selective inhibitors of chemokine-"Glyceptor" sequence binding from a diverse or even structurally similar group of molecules.

Example 8B

Demonstration of Growth Factor-"Glyceptor" sequence Binding Inhibition with Synthetic "Glyceptor" sequence Antagonists The assay may be used essentially as described above to identify effective inhibitors of growth factor-"Glyceptor" sequence binding. As before, optimal conditions for the assay are determined by the measured binding affinity of a "Glyceptor" sequence for its growth factor or cytokine. Once this has been done, the assay is set up as above. In the case of bFGF, the concentration of the protein used typically will be greater than 2–5 nM and in the case of platelet derived growth factor A, long form (PDGF-AA) will be 5 nM or greater. The growth factors or cytokines may be obtained from commercial sources or may be made by means well known to those skilled in the art. "Glyceptor" sequences may be isolated from radiolabeled heparin or heparan sulfate from appropriate sources using preparative ACE as described above.

The screening assay then is conducted as follows. Each compound within an appropriate library of compounds is suspended in an appropriate buffer, e.g. PBS, to a final concentration of about 100 µM. Twenty to fifty µl of each compound solution is added to the 0.5 ml of buffer containing radiolabeled "Glyceptor" sequence prior to the addition of the growth factor or cytokine solution. 0.5 ml of the growth factor or cytokine solution is then added and incubation is carried out as above. The final concentration of the compound to be tested is thus 20–50 µM in the final assay mixture. This concentration may be raised or lowered to increase or decrease the stringency of the screening assay.

Figure 10A:
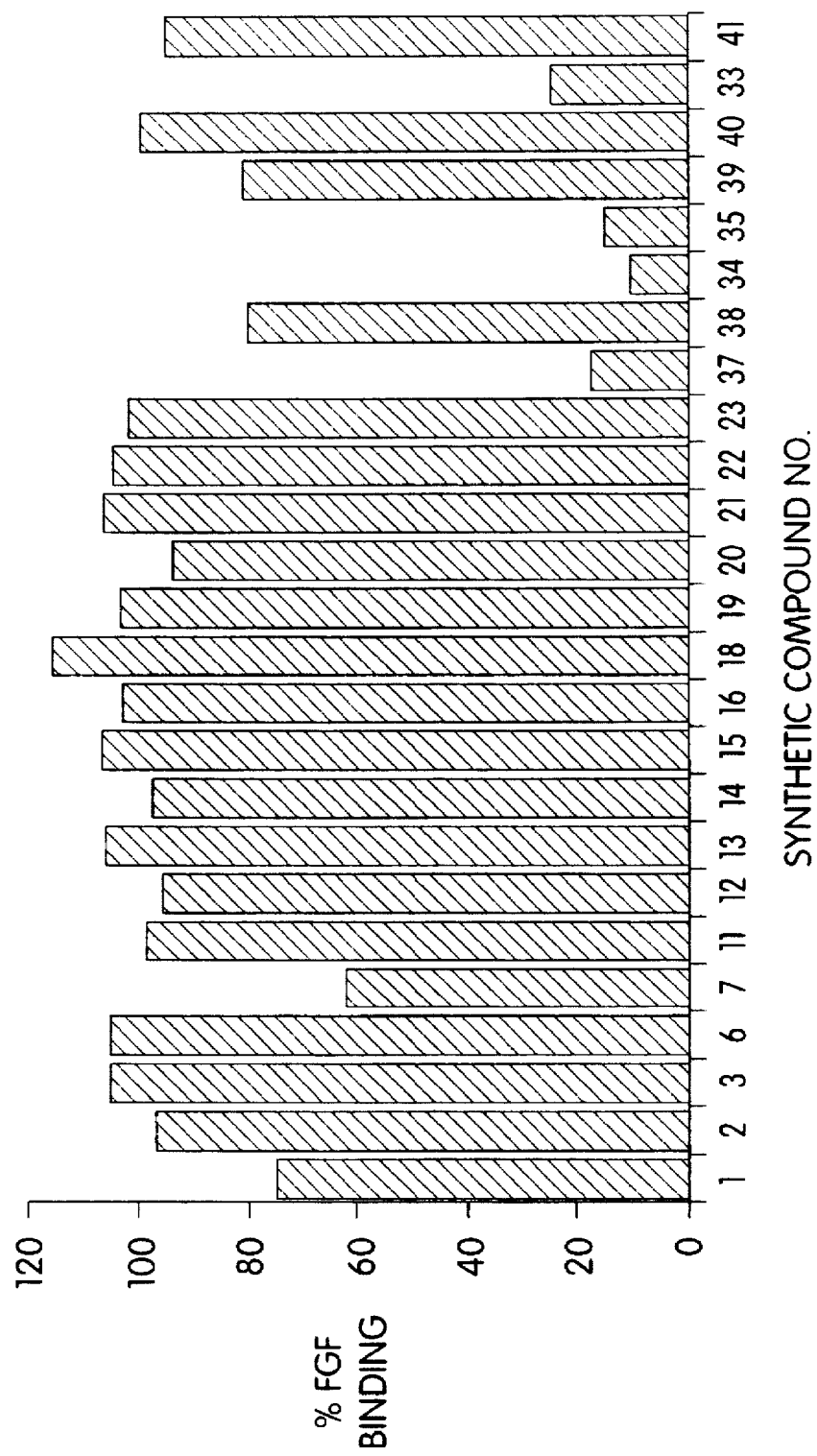
FIG. 10A graphs the inhibitory effect of 25 different polysulfonated naphthylurea compounds on FGF- "Glyceptor" sequence binding.
Figure 11:
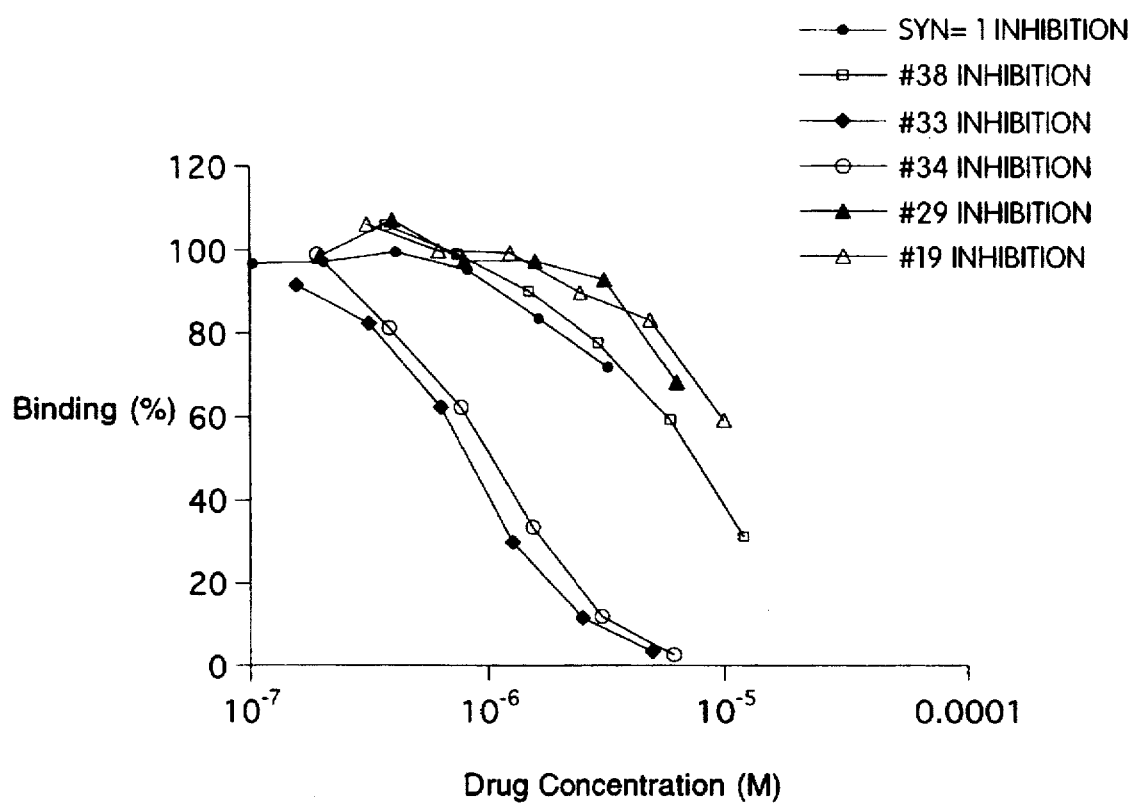
FIG. 11 compares the inhibitory effect of various "Glyceptor" sequence analogs on FGF-"Glyceptor" sequence binding, replotted to highlight the analog concentration required for 50% inhibition. In the figure, Syn #33 and Syn #34 show the greatest affinity (only $10^{-6}$M required for 50% inhibition.)

As an example, a collection of 25 different synthetic polysulfonated naphthylurea molecules having certain structural features characteristic of heparan sulfate were screened for "Glyceptor" sequence antagonists using an assay as described above. The results, shown in FIGS. 10A and 10B compare the effectiveness of the various compounds in blocking "Glyceptor" sequence binding to two growth factors: bFGF-"Glyceptor" sequence binding relative to PDGF-AA-"Glyceptor" sequence binding. As can be seen from the figures, some compounds effectively inhibit the binding of both growth factors to their "Glyceptor" sequences (Syn #34, Syn #35), while other compounds effectively inhibit only one of the ligands (Syn #20, Syn #39.) The data demonstrate the ability of the "Glyceptor" sequence screening assay to identify selective inhibitors of growth factor-"Glyceptor" sequence binding from a diverse but structurally similar group of molecules. FIG. 11 replots the data for various synthetic analogs and FGF, clearly demonstrating the differential affinities of the analogs for the growth factor, and also provides a means for determining the quantity required for half maximum (50%) inhibition activity.

Example 8C

In an alternative screening method, oligosaccharide fragments derived from appropriate tissues or cultured cells may be passed over an affinity matrix as described above. Non-bound and weakly bound oligosaccharides are removed. The tightly bound GAG sequence is eluted from the affinity material may be characterized as necessary, using stand means (see, for example, Turnbull et al. (1992) J. Biol. Chem. 267:7–10341 and Habuchi, et al. (1992) Biochem. J. 285:805–813.) The stripped matrix next is used to screen for binding compounds from a random library, such as may be formed using peptides, oligonucleotides, oligosaccharides, and low molecular weight or other compounds and natural products. Non-binding and weakly binding compounds are washed from the matrix while compounds which tightly bind to any surface on the ligand remain associated. With a sufficiently large library of compounds the entire ligand surface may be expected to select compounds which bind with reasonably high affinity. The select group of compounds which specifically bind to the GAG binding domain of the ligand are eluted from the affinity matrix using the previously produced tight binding GAG sequence. Compounds not specifically displaced by the oligosaccharide containing the selected sequence remain bound to the matrix and are discarded. The specifically bound compounds are characterized and evaluated for their ability to displace ligand bound to proteoglycan under physiological conditions. The optimal compound may be viewed as lead compounds for drug development. These lead compounds then can be tested for their efficacy in clinical applications by determining their therapeutic indices using standard means well known in the art.

Example 9
"Glyceptor" sequence binding domains of chemokines and utility in "Glyceptor" sequence antagonist/ligand antagonist rational drug design.

The sequence of IL-8 has been reported (e.g. see Miller and Krangle (1992) Crit. Reviews Immunology 12:17–46). The amino acid sequence corresponding to the soluble form of the protein is presented in Seq.ID No. 1. A high degree of homology (amino acid identity) is evident between all known members of the chemokine family (also known as the platelet factor 4 superfamily and also referred to in the literature as "intercrines"). Three regions within the primary structure of each molecule participate in the binding of the oligodisaccharide unit that defines the "Glyceptor" sequence interaction site. Using the numbering systems based on the 72 amino acid form of IL-8 (as described in Miller et al., above), these three regions can be identified as follows:
Region 1—amino acids from Lys15 through Lys20
Region 2—amino acids from Ser44 through Glu 48
Region 3—amino acids from Lys54 through Ser 72
These regions in IL-8 can readily be recognized by their homology in the other members of the superfamily and thus identified and localized by a simple comparison. In addition to the chemokines listed in Miller et al., other chemokine sequences may be found in the future, and their relevant amino acid sequences aligned for example, as disclosed in Oppenheim et al. (1991) *Ann Rev. Immunol* 9: 617–648. A general structure of the proteins and the location of Regions 1, 2, 3 also can be identified in Oppenheim et al. using the information disclosed herein.

Regions 1 and 2 within the family members share relatively high amino acid sequence homology, and Region 3 shows the greatest degree of amino acid variability, the combination of which provide sequence and structural specificity of a given chemokine for its "Glyceptor" sequence. The C-terminal amino acid sequences (Region 3) for four different chemokines: IL8, PF4, NAP2 and GROα, (Seq. ID Nos. 1–4, respectively), are presented in FIG. 4, aligned as presented in Oppenheim et al. The sequence shown in FIG.4 for IL8 coresponds to residues 50–72 of Seq. ID No.1.

These three regions, by virtue of the fact that they represent the domains which contact the "Glyceptor" sequence chains as well as being the domains which provide specificity of binding, are preferred targets for the development of antagonists of "Glyceptor" sequence binding. For example, and as demonstrated herein, glycan binding specificity differs between the chemokines PF4 and IL-8. A comparison of the homologies in Region 3 identifies the presence of glutamic acid at a position occupied by lysine in PF4 (see FIG. 4).

Example 10
Generation of a Combinatorial Library of Compounds with Structural Features in Common with Heparan Sulfate As may be seen from the structural features of the "Glyceptor" sequence binding region on the surface of a chemokine and as described in Example 9, the "Glyceptor" sequence binds in an extended or semi-extended fashion to a region defined by an array of basic side chains on the protein. The molecular dimensions of this binding region may be used to guide the design of a combinatorial library of compounds, which may also incorporate functional groups designed to interact with the known residues in the "Glyceptor" sequence binding site, including anionic groups to interact with one or more of the basic side chains defining said binding site. Such a "directed" library will contain more highly effective antagonists at a higher frequency than a random library. "Glyceptor" sequence screening assays as described above may be used to identify the most potent antagonists from within the directed library.

A preferred molecular scaffolding or backbone for the library will consist of an oligomeric structure which permits the linear combination of a set of defined monomeric building blocks. The oligomeric nature of the generic backbone provides a set of compounds which have the general characteristic of binding in an extended fashion across the protein surface rather than fitting into a pocket, cleft, or groove in the protein which will be a preferred feature of a "Glyceptor" sequence antagonist. While peptide synthetic approaches are particularly well known for producing oligomeric structures (see for example Houghten et al., (1991) *Nature* 354: 84), many other approaches may be utilized including N-alkylated glycine, polyaminimide (*Eur. J. Med. Chem.—Chem. Ther.* (1982) 17: 265) (Simon R. J. et al. *Proc. Nat. Acad. Sci.* USA 89: 9367 (1992), polydeoxyribose phosphate (Ellington, et al. (1992) *Nature* 355: 850), and polyribose phosphate (Ellingon et al. (1990) *Nature* 346: 818), the disclosures of which are incorporated herein by reference. As will be apparent to those skilled in the art, there are other approaches for producing combinatorial libraries of linear oligomeric structures all of which will be useful in the practice of the invention.

The monomer building blocks utilized in the synthesis of the oligomeric structures will contain groups or side chains pendant from them which have structural features that can interact with residues in the glycan-binding protein-binding site which may include sulfate esters or sulfonate groups, phosphates, carboxylate functions, amino, and hydroxyl groups as well as hydrophobic moieties. These may be directly attached to the monomer itself or may be attached to a linking/spacing group such as an aromatic ring or an aliphatic chain. Monomers containing appropriate pendant structures may be synthesized by techniques well known to those skilled in the art. The actual nature of the monomer and the procedure for the chemical synthesis will depend on the oligomer structure selected for the combinatorial library.

Figures 4, 5:
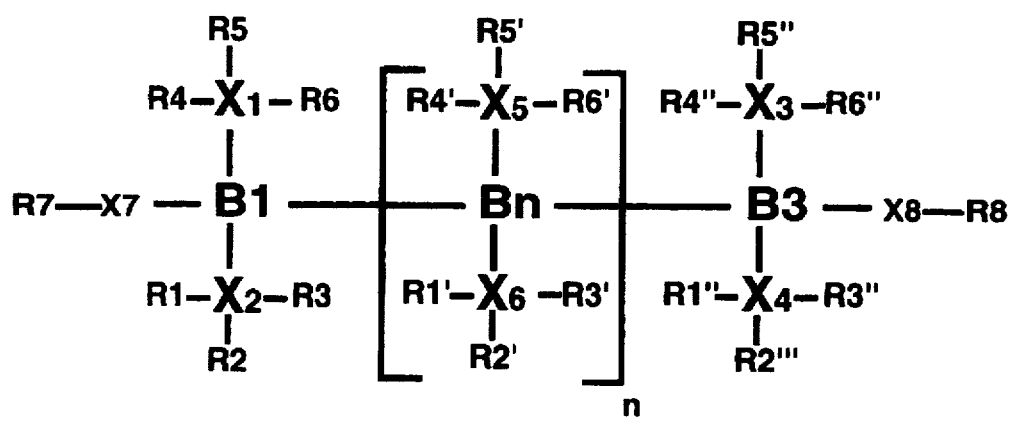
FIG. 4 compares the C-terminal amino acid sequences containing the putative "Glyceptor" sequence binding regions for four chemokines.
FIG. 5 describes a generic chemical structure defining a class of synthetic organics useful in the rational design of a "Glyceptor" sequence antagonist.
Figure 6C:
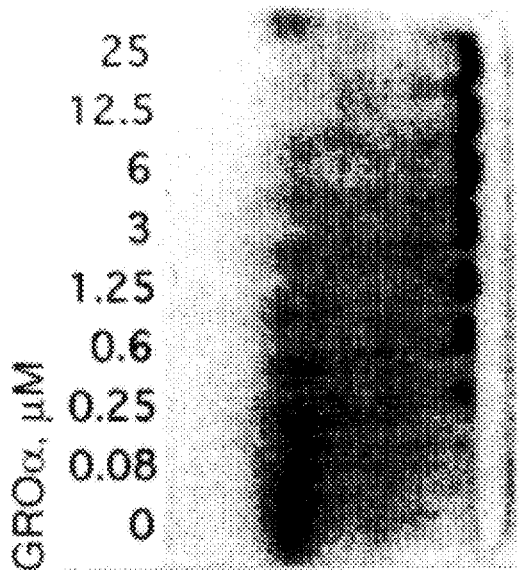
FIG. 6A–D is a photomicrograph of the binding pattern generated by affinity coelectrophoresis of four chemokines: PF4 (FIG. 6A), IL-8(FIG. 6B), GROα(FIG. 6C) and NAP2 (FIG. 6D) with heparin.
Figure 6A:
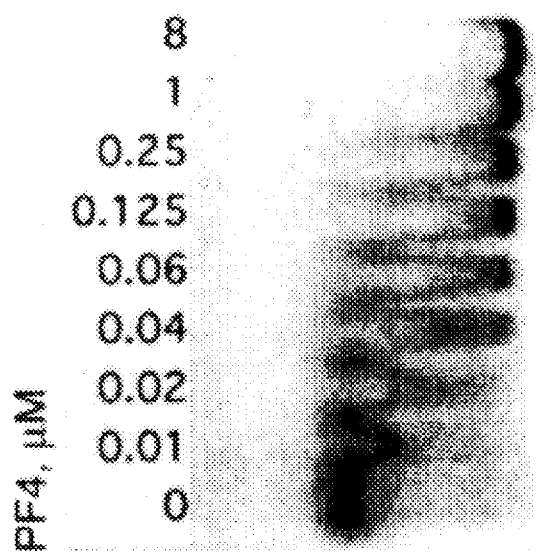
Figure 6D:
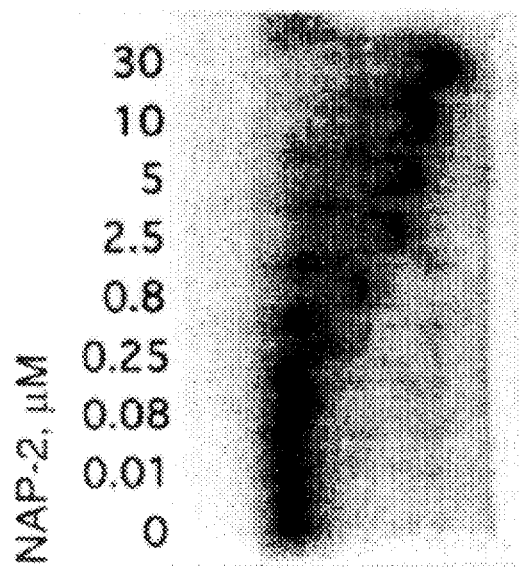
Figure 6B:
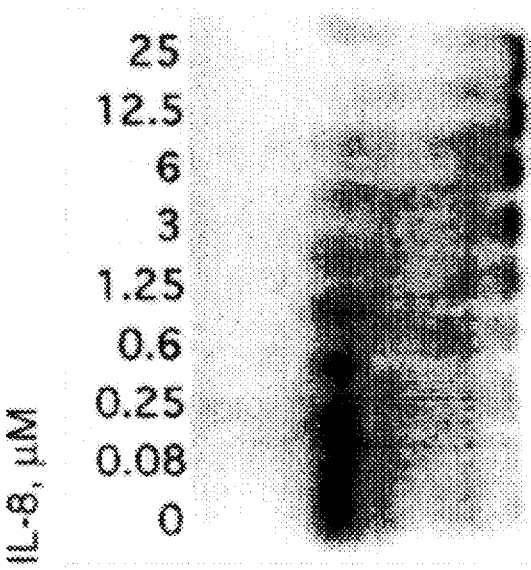
Figure 7A:
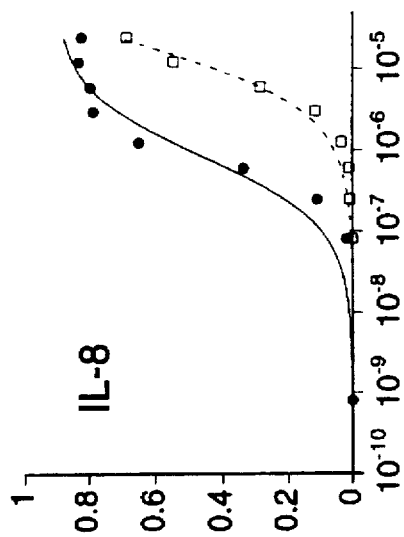
FIG. 7A–D are plots of the binding affinity for four chemokines: PF4 (FIG. 7A), IL-8(FIG. 7B), GROα(FIG. 7C) and NAP2(FIG. 7D) for high affinity heparin (HA, closed circles) and low affinity heparin (open squares)
Figure 7B:
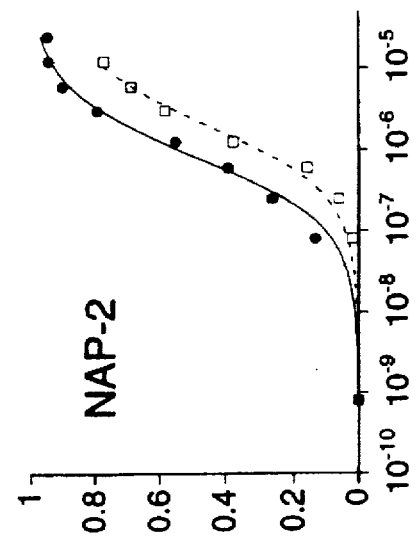
Figure 7C:
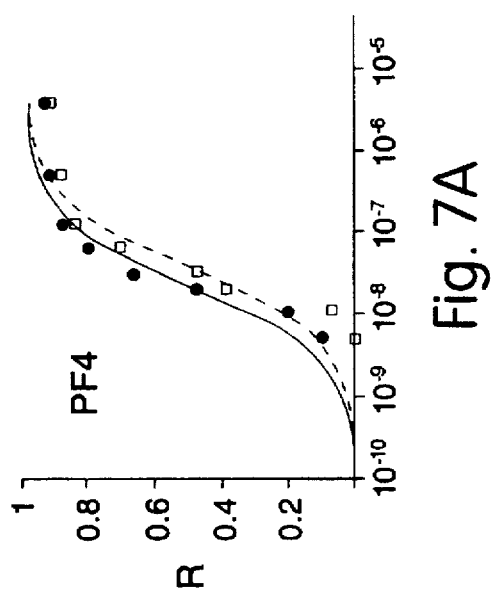
Figure 7D:
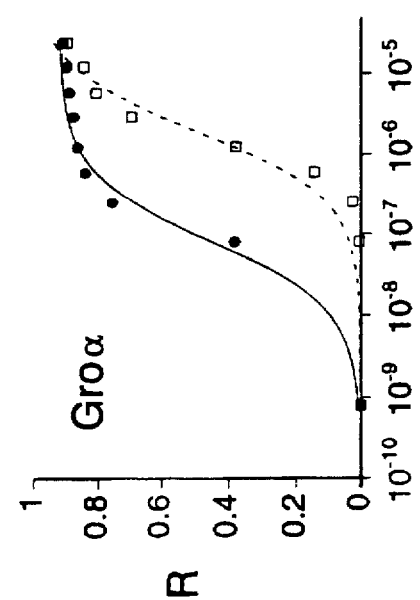

A generic structure defining the features of the synthetic oligomers useful as candidate glycosaminoglycan analogs to be tested as described herein is presented in FIG. 5 and described in detail hereinabove. Using the generic structure, a hexameric library is constructed using an N-alkylated glycine backbone (e.g., an oligomer composed of six monomeric backbone units, all of which are N-alkylated glycines. See, for example, Simon et al. *PNAS* (1992) 89: 9367), and each monomeric unit containing one of five possible different functional groups. Possible functional groups pendant from the monomer units are selected from
—$CH_2$—$SO_3^-$; —$CH_2CH_2OH$;
—$CH_2CH_2$—$NH_2$; —$CH_2$—$CH_2COOH$; —$C_6H_5$—$OS_3^-$.

The diversity of this library is thus 15,625 compounds ($5^6$). Screening assays reasonably can be performed on each candidate compound as described herein to identify those candidiates having reasonable potency in blocking a specific glycan-binding protein-"Glyceptor" sequence interaction. The screening assays can be performed without undue experimentation, using standard molecular and cell biology tools in common use in the art. For example, screening assays can be performed in standard 96-well plates. Fifteen such plates reasonably can be set up at a time to perform multiple screening assays in parallel. Thus, with only 10–11 reiterations of the screening assay all 15,625 compounds can be screened for their binding affinity for a given glycan-binding protein. Even allowing for a maximum incubation time of 2 hours, all compounds reasonably can be assayed in a matter of days. Compounds selected according to the screening assay exemplified in Example 8 will be expected to function as effective "Glyceptor" sequence antagonists.

In a combinatorial library of the size described here, 1–2% of the candidate protein-specific glycosaminoglycan sequences reasonably can be expected to have a binding affinity for a given glycan-binding protein above the threshold level of $10^{-6}$M. Of course, larger libraries can be expected to produce greater yields of specific, high affinity analogs.

Example 11
Preparation of a "Decoy Ligand" for Inhibition of IL-8 Action In Vivo IL-8 requires a tripeptide sequence, glu-leu-arg (ELR), near the amino terminus for interaction with the signaling receptor on leukocytes. Deletion of this sequence results in the loss of binding to the leukocyte receptor and the concomitant inability to activate neutrophils (Clark-Lewis et al., (1991) *J. Biol. Chem.* 266: 23128). Removal or deletion of this sequence does not however, alter the ability of the IL-8 molecule to bind to its cognate "Glyceptor" sequence.

A mutant IL-8 gene is synthesized in which the ELR sequence at positions 4–6 (Seq. ID No. 1) is modified to glu-leu-gln (ELQ). The modified gene is expressed in *E. coli* by standard techniques well known to those skilled in the art and the protein product is extracted from the lysed cell pellet with 6M guanidine-HCl. The extract is dialyzed against 50 mM Tris, 0.125M NaCl and passed over a heparin-agarose column. The ELQ-IL-8 bound to the heparin-agarose column under these conditions then is selectively eluted with a gradient of NaCl ranging from 0.125M up to 1M. The mutant chemokine is eluted from the column at about 0.6–0.7M salt.

Consistent with previous studies, the ELQ-IL-8 is not able to activate or attract neutrophils. When studied by affinity coelectrophoresis, however, ELQ-IL-8 behaves in a similar fashion to native IL-8 with regard to binding to heparin and heparan sulfate. Moreover, ELQ-IL-8 can compete with native IL-8 for binding to the IL-8 "Glyceptor" sequence and, thus, is an effective competitive inhibitor of IL-8-"Glyceptor" sequence binding.

The ability of ELQ-IL-8 to function as a competive inhibitor of IL-8 binding and thus serve as a "decoy ligand" can be demonstrated as follows. A sample of human dermal tissue of about 1 mm³ is incubated with $^{125}$I-labeled human IL-8 as described in the art (see, e.g., Rot. A. (1992) *Cytokine* 4, 347, the disclosure of which is incorporated herein by reference). Microscopic autoradiography reveals that the IL-8 binds preferentially to certain regions of the vasculature, for example, the post-capillary venules. When ELQ-IL-8 is added in a 10 fold excess over the radiolabeled native IL-8, the binding of the labeled native IL-8 is substantially reduced. The data demonstrate that ELQ-IL-8 can function to block binding of native IL-8 to "Glyceptor" sequences ex vivo and also reveals that ELQ-Il-8 can be an effective inhibitor of endogenous IL-8 in vivo.

Example 12
Targeting of agents to a specific "Glyceptor" sequence

Specific "Glyceptor" sequences may be used for delivery of agents to selected sites in the body. Such targeting is useful when it is desirable to produce a locally high concentration of, for example, a therapeutic drug (e.g., a cytotoxin at a tumor locus) or an imaging agent.

Because ELQ-IL-8 lacks the capacity to attract and/or activate neutrophils it is anticipated to be a relatively benign agent for clinical use. In addition, as described above, ELQ-IL-8 can selectively displace native IL-8 from the IL-8 "Glyceptor" sequence localized on post-capillary endothelium. ELQ-IL-8 was tested for its ability to bind directly to "Glyceptor" sequences on post-capillary endothelium by labeling the mutant chemokine with $^{125}$I and studying binding as described above. Binding occurs in the same pattern as observed with native IL-8. The data demonstrate that site-specific delivery of agents can be achieved using tissue-specific "Glyceptor" sequences and ligand antagonists.

Example 13
Chimeric protein-specific glycosaminoglycan sequences

Useful protein-specific glycosaminoglycan sequence analogs may include chimeric molecules comprising at least two covalently linked "Glyceptor" sequences described herein below. The chimeric may be created as a single molecule or, alternatively, two separate "Glyceptor" sequences can be chemically crosslinked in vitro. The crosslinker also may comprise a spacer or "bridge" sequence of a defined length (e.g., of about 1–20 atoms in a linear array) to prevent steric interference of the two sequences. Chemical spacer and linker sequences well known in the chemical arts and shown to be advantageous in vivo include sulfhydryl-specific crosslinking reagents such as the bifunctional crosslinking reagent bismaleimidohexane (BMH), a water insoluble linker that can be obtained from Pierce, Rockford, Ill., and heterobifunctional crosslinking agents, including 4-succinimidyloxycarbonyl-methyl-(2-pyridyldithio)-toluene (SMPT) or N-succinimidyl-3-(2-pyridyldithio)propionate (SPDP), both of which can be obtained from Pierce, Rockland, Ill. Another linker known in the art includes a peptide bridge, such as the water soluble bismaleimidocaproyl amino acid (MCA) linker.

Example 14
Glycosaminoglycan and ligand analogs as in vivo imaging agents

Particular analogs may have utility as in vivo imaging agents wherein the "Glyceptor" sequence analog or ligand analog is complexed with a detectable moiety, preferably one comprising a radioactive moiety. A preferred remotely detectable moiety for in vivo imaging includes the radioactive atom Technetium$^{-99m}$ ($^{99m}$Tc), a gamma emitter with a half-life of about 6 hours. Non-radioactive moieties also useful in imaging include nitroxide spin labels as well as lanthanide and transition metal ions all of which induce proton relaxation in situ. In addition to immunoimaging, the complexed radioactive moieties may be used in standard radioimmunotherapy protocols to destroy the targeted cell. Preferred nucleotides for high dose radioimmunotherapy include the radioactive atoms $^{90}$Yttrium ($^{90}$Yt), $^{131}$Iodine ($^{131}$I) and $^{111}$Indium ($^{111}$In). These moieties all are well described in the art, as are methods for their attachment to a targeting molecule, methods for their detection, and descriptions of their physical charateristics.

The method may be used to advantage, for example, to target an imaging agent to an endothelial luminal surface, e.g., to monitor the degree of inflammation in a mammal. Here the targeting agent is a protein-specific glycosaminoglycan sequence having preferential binding affinity for a surface bound protein, preferably a selectin. Alternatively, a modified soluble effector ligand capable only of binding an immobilized glycosaminoglycan may be used as the targeting agent.

Example 15
Glycosaminoglycan and ligand analogs as In vivo targeting agents

The invention also contemplates the use of analogs for targeting therapeutic agents to a locus in vivo. Examples of pharmacologically active drugs, particularly suited to a targeting protocol, include molecules that inhibit cell proliferation and cytotoxic agents that kill cells. Other, useful molecules may include toxins, for instance, the toxic portion of the Pseudomonas exotoxin, phytolaccin, ricin, ricin A chain, or diptheria toxin, or other related proteins known as ricin A chain-like ribosomal inhibiting proteins, i.e., proteins capable of inhibiting protein synthesis at the level of the ribosome, such as pokeweed antiviral protein, gelonin, and barley ribosomal protein inhibitor.

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for modulating the activity of a ligand selected from the group consisting of a chemokine ligand, a growth factor ligand, a lipoprotein ligand and an amyloid protein ligand, said ligand having a first binding site specific for a cell surface receptor and a second binding site specific for a glycosaminoglycan sequence, said method comprising the step of contacting said ligand with a glycosaminoglycan sequence analog, said analog being identified by a method comprising:

providing said ligand and a glycosaminoglycan sequence having a known binding specificity for said ligand;

providing a candidate glycosaminoglycan sequence analog, said candidate analog being a synthetic molecule that mimics a naturally-occurring glycosaminoglycan sequence, and said candidate analog having a predetermined composition other than polysulfonated naphthylurea;

combining said ligand, said glycosaminoglycan sequence and said candidate analog under conditions to promote binding of said ligand to said glycosaminoglycan sequence to form a complex;

determining the ability of said candidate analog to compete with said glycosaminoglycan sequence for binding to said ligand with a half maximum inhibition activity of less than about $1\times10^{-6}$M; and isolating said analog.

2. The method of claim 1 wherein said ligand is a chemokine ligand.

3. The method of claim 2 wherein said chemokine ligand and said glycosaminoglycan sequence are provided under conditions to promote binding of said chemokine ligand and said glycosaminoglycan sequence to form a complex.

4. The method of claim 2 wherein said chemokine ligand and said candidate analog first are combined under conditions to promote binding of said chemokine ligand and said analog to form a complex before being combined with said glycosaminoglycan sequence.

5. The method of claim 2 wherein said synthetic molecule is an oligodisaccharide.

6. The method of claim 2 wherein said analog binding to said chemokine ligand inhibits activation of circulating leukocytes.

7. The method of claim 2 wherein said analog binding to said chemokine ligand inhibits an inflammatory response.

8. The method of claim 2 wherein said chemokine ligand is selected from the group consisting of PF4, IL8, PBP, CTAP III, NAP-2, GRO$\alpha$, GRO$\beta$, GRO$\gamma$, $\beta$-Thromboglobulin, ENA-78, $\gamma$IP10, MCP1-3, MCAF, RANTES, LD78, ACT-2 and I1309.

9. The method of claim 1 wherein said ligand is a growth factor ligand.

10. The method of claim 9 wherein said growth factor ligand and said glycosaminoglycan sequence are provided under conditions to promote binding of said growth factor ligand and said glycosaminoglycan sequence to form a complex.

11. The method of claim 9 wherein said growth factor ligand and said candidate analog first are combined under conditions to promote binding of said growth factor ligand and said analog to form a complex before being combined with said glycosaminoglycan sequence.

12. The method of claim 9 wherein said synthetic molecule is an oligodisaccharide.

13. The method of claim 9 wherein said growth factor ligand is selected from the group consisting of PDGF, HGF, VEGF, int-2, hst/KFGF, FGF-5, KGF, IL-3 and GMSF.

14. The method of claim 9 wherein said analog binding to said growth factor ligand inhibits cell proliferation.

15. The method of claim 9 wherein said analog binding to said growth factor ligand inhibits a hyperproliferative disease.

16. The method of claim 1 wherein said ligand is a lipoprotein ligand.

17. The method of claim 16 wherein said lipoprotein ligand and said glycosaminoglycan sequence are provided under conditions to promote binding of said lipoprotein ligand and said glycosaminoglycan sequence to form a complex.

18. The method of claim 16 wherein said lipoprotein and said candidate analog first are combined under conditions to promote binding of said lipoprotein ligand and said analog to form a complex before being combined with said glycosaminoglycan sequence.

19. The method of claim 16 wherein said synthetic molecule is an oligodisaccharide.

20. The method of claim 16 wherein said lipoprotein ligand is selected from the group consisting of the enzymes LPL, MTGL, and ECSOD, and the lipid transport proteins, Apolipoprotein B-100 and Apolipoprotein E.

21. The method of claim 1 wherein said ligand is an amyloid protein ligand.

22. The method of claim 21 wherein said amyloid protein ligand and said glycosaminoglycan sequence are provided under conditions to promote binding of said amyloid protein ligand and said glycosaminoglycan sequence to form a complex.

23. The method of claim 21 wherein said amyloid protein and said candidate analog first are combined under conditions to promote binding of said amyloid protein ligand and said analog to form a complex before being combined with said glycosaminoglycan sequence.

24. The method of claim 21 wherein said synthetic molecule is an oligodisaccharide.

25. A method for modulating the activity of a ligand selected from the group consisting of a chemokine ligand, a growth factor ligand, a lipoprotein ligand and an amyloid protein ligand, said ligand having a first binding site specific for a cell surface receptor and a second binding site specific for a glycosaminoglycan sequence, said method comprising the step of contacting said ligand with a glycosaminoglycan sequence analog, said analog being identified by a method comprising:

providing said ligand and a glycosaminoglycan sequence having a known binding specificity for said ligand;

providing a candidate glycosaminoglycan sequence analog selected from a combinatorial chemical library, said candidate analog having a predetermined composition other than polysulfonated naphthylurea;

combining said ligand, said glycosaminoglycan sequence and said candidate analog under conditions to promote binding of said ligand to said glycosaminoglycan sequence to form a complex;

determining the ability of said candidate analog to compete with said glycosaminoglycan sequence for binding to said ligand with a half maximum inhibition activity of less than about $1\times10^{-6}$M; and isolating said analog.

26. The method of claim 25 wherein said ligand is a chemokine ligand.

27. The method of claim 26 wherein said chemokine ligand and said glycosaminoglycan sequence are provided under conditions to promote binding of said chemokine ligand and said glycosaminoglycan sequence to form a complex.

28. The method of claim 26 wherein said chemokine ligand and said candidate analog first are combined under conditions to promote binding of said chemokine ligand and said analog to form a complex before being combined with said glycosaminoglycan sequence.

29. The method of claim 26 wherein said analog binding to said chemokine ligand inhibits activation of circulating leukocytes.

30. The method of claim 26 wherein said analog binding to said chemokine ligand inhibits an inflammatory response.

31. The method of claim 26 wherein said chemokine ligand is selected from the group consisting of PF4, IL8, PBP, CTAP III, NAP-2, GRO$\alpha$, GRO$\beta$, GRO$\gamma$, $\beta$-Thromboglobulin, ENA-78, $\gamma$IP10, MCP1-3, MCAF, RANTES, LD78, ACT-2 and I309.

32. The method of claim 25 wherein said ligand is a growth factor ligand.

33. The method of claim 32 wherein said growth factor ligand and said glycosaminoglycan sequence are provided under conditions to promote binding of said growth factor ligand and said glycosaminoglycan sequence to form a complex.

34. The method of claim 32 wherein said growth factor ligand and said candidate analog first are combined under conditions to promote binding of said growth factor ligand and said analog to form a complex before being combined with said glycosaminoglycan sequence.

35. The method of claim 32 wherein said growth factor ligand is selected from the group consisting of PDGF, HGF, VEGF, int-2, hst/KFGF, FGF-5, KGF, IL-3 and GMSF.

36. The method of claim 32 wherein said analog binding to said growth factor ligand inhibits cell proliferation.

37. The method of claim 32 wherein said analog binding to said growth factor ligand inhibits a hyperproliferative disease.

38. The method of claim 25 wherein said ligand is a lipoprotein ligand.

39. The method of claim 38 wherein said lipoprotein ligand and said glycosaminoglycan sequence are provided under conditions to promote binding of said lipoprotein ligand and said glycosaminoglycan sequence to form a complex.

40. The method of claim 38 wherein said lipoprotein and said candidate analog first are combined under conditions to promote binding of said lipoprotein ligand and said analog to form a complex before being combined with said glycosaminoglycan sequence.

41. The method of claim 38 wherein said lipoprotein ligand is selected from the group consisting of the enzymes LPL, MTGL, and ECSOD, and the lipid transport proteins, Apolipoprotein B-100 and Apolipoprotein E.

42. The method of claim 25 wherein said ligand is an amyloid protein ligand.

43. The method of claim 42 wherein said amyloid protein ligand and said glycosaminoglycan sequence are provided under conditions to promote binding of said amyloid protein ligand and said glycosaminoglycan sequence to form a complex.

44. The method of claim 42 wherein said amyloid protein and said candidate analog first are combined under conditions to promote binding of said amyloid protein ligand and said analog to form a complex before being combined with said glycosaminoglycan sequence.

45. A method for modulating the activity of a ligand selected from the group consisting of a chemokine ligand, a growth factor ligand, a lipoprotein ligand and an amyloid protein ligand, said ligand having a first binding site specific for a cell surface receptor and a second binding site specific for a glycosaminoglycan sequence, said method comprising the step of contacting said ligand with a glycosaminoglycan sequence analog, said analog being identified by a method comprising:

providing said ligand and a glycosaminoglycan sequence having a known binding specificity for said ligand;

providing a candidate glycosaminoglycan sequence analog, said candidate analog being a natural-sourced glycosaminoglycan sequence, and said candidate analog having a predetermined composition other than polysulfonated naphthylurea;

combining said ligand, said glycosaminoglycan sequence and said candidate analog under conditions to promote binding of said ligand to said glycosaminoglycan sequence to form a complex;

determining the ability of said candidate analog to compete with said glycosaminoglycan sequence for binding to said ligand with a half maximum inhibition activity of less than about $1\times10^{-6}$M; and isolating said analog.

46. The method of claim 45 wherein said ligand is a chemokine ligand.

47. The method of claim 46 wherein said chemokine ligand and said glycosaminoglycan sequence are provided under conditions to promote binding of said chemokine ligand and said glycosaminoglycan sequence to form a complex.

48. The method of claim 46 wherein said chemokine ligand and said candidate analog first are combined under conditions to promote binding of said chemokine ligand and said analog to form a complex before being combined with said glycosaminoglycan sequence.

49. The method of claim 46 wherein said natural-sourced glycosaminoglycan sequence is derived from a source selected from the group consisting of liver, skin, lymph nodes, intestinal mucosa, thymus and synovial tissue.

50. The method of claim 46 wherein said analog binding to said chemokine ligand inhibits activation of circulating leukocytes.

51. The method of claim 46 wherein said analog binding to said chemokine ligand inhibits an inflammatory response.

52. The method of claim 46 wherein said chemokine ligand is selected from the group consisting of PF4, IL8, PBP, CTAP III, NAP-2, GROα, GROβ, GROγ, β-Thromboglobulin, ENA-78, γIP10, MCP1-3, MCAF, RANTES, LD78, ACT-2 and I309.

53. The method of claim 45 wherein said ligand is a growth factor ligand.

54. The method of claim 53 wherein said growth factor ligand and said glycosaminoglycan sequence are provided under conditions to promote binding of said growth factor ligand and said glycosaminoglycan sequence to form a complex.

55. The method of claim 53 wherein said growth factor ligand and said candidate analog first are combined under conditions to promote binding of said growth factor ligand and said analog to form a complex before being combined with said glycosaminoglycan sequence.

56. The method of claim 53 wherein said natural-sourced glycosaminoglycan sequence is derived from a source selected from the group consisting of tumors and placenta.

57. The method of claim 53 wherein said growth factor ligand is selected from the group consisting of PDGF, HGF, VEGF, int-2, hst/KFGF, FGF-5, KGF, IL-3 and GMSF.

58. The method of claim 53 wherein said analog binding to said growth factor ligand inhibits cell proliferation.

59. The method of claim 53 wherein said analog binding to said growth factor ligand inhibits a hyperproliferative disease.

60. The method of claim 45 wherein said ligand is a lipoprotein ligand.

61. The method of claim 60 wherein said lipoprotein ligand and said glycosaminoglycan sequence are provided under conditions to promote binding of said lipoprotein ligand and said glycosaminoglycan sequence to form a complex.

62. The method of claim 60 wherein said lipoprotein and said candidate analog first are combined under conditions to promote binding of said lipoprotein ligand and said analog to form a complex before being combined with said glycosaminoglycan sequence.

63. The method of claim 60 wherein said natural-sourced glycosaminoglycan sequence is derived from liver.

64. The method of claim 60 wherein said lipoprotein ligand is selected from the group consisting of the enzymes LPL, MTGL, and ECSOD, and the lipid transport proteins, Apolipoprotein B-100 and Apolipoprotein E.

65. The method of claim 45 wherein said ligand is an amyloid protein ligand.

66. The method of claim 65 wherein said amyloid protein ligand and said glycosaminoglycan sequence are provided under conditions to promote binding of said amyloid protein ligand and said glycosaminoglycan sequence to form a complex.

67. The method of claim 65 wherein said amyloid protein and said candidate analog first are combined under conditions to promote binding of said amyloid protein ligand and said analog to form a complex before being combined with said glycosaminoglycan sequence.

* * * * *

UNITED STATES PATENT AND TRADEMARK OFFICE
CERTIFICATE OF CORRECTION

PATENT NO. : 5,795,860
DATED : August 18, 1998
INVENTOR(S) : Witt et al.

It is certified that error appears in the above-identified patent and that said Letters Patent is hereby corrected as shown below:

On the title page, Item [54],

Delete the entire Title, and insert

--METHODS FOR MODULATING LIGAND ACTIVITY USING GLYCOSAMINOGLYCAN SEQUENCE ANALOGS--.

[57] Delete the entire text of the Abstract, and insert in its place the following:

-- Disclosed are methods for modulating the activity of chemokine, growth factor, lipoprotein and amyloid protein ligands having a first binding site specific for a cell surface receptor and a second binding site specific for a glycosaminoglycan sequence analog, by contacting the ligand with a glycosaminoglycan sequence analog. Useful glycosaminoglycan analogs may be synthetic molecules, natural-sourced molecules and/or members of a combinatorial library. --

Signed and Sealed this

Sixth Day of July, 1999

*Attest:*

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 72 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 1..72
      ( D ) OTHER INFORMATION: /label= IL- 8
        / note= "OPPENHEIM ET AL. (1991) ANN. REV. IMMUNOL. 9:617-648"

( x i ) SEQUENCE DESCRIPTION: SEQ ID NO:1:

```
Ser Ala Lys Glu Leu Arg Cys Gln Cys Ile Lys Thr Tyr Ser Lys Pro
 1               5                  10                  15

Phe His Pro Lys Phe Ile Lys Glu Leu Arg Val Ile Glu Ser Gly Pro
                20                  25                  30

His Cys Ala Asn Thr Glu Ile Ile Val Lys Leu Ser Asp Gly Arg Glu
                35                  40                  45

Leu Cys Leu Asp Pro Lys Glu Asn Trp Val Gln Arg Val Val Glu Lys
            50                  55                  60

Phe Leu Lys Arg Ala Glu Asn Ser
65                  70
```

( 2 ) INFORMATION FOR SEQ ID NO:2:

( i ) SEQUENCE CHARACTERISTICS:
      ( A ) LENGTH: 19 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein -continued (B) LOCATION: 1..19
(D) OTHER INFORMATION: /label=PF4
   / note= "OPPENHEIM ET AL. (1991) ANN. REV. IMMUNOL.
   9:617-648"

(xi) SEQUENCE DESCRIPTION: SEQ ID NO:2:

Cys Leu Asp Leu Gln Ala Pro Leu Tyr Lys Lys Ile Ile Lys Lys Leu
1               5                   10                  15

Leu Glu Ser (2) INFORMATION FOR SEQ ID NO:3:

(i) SEQUENCE CHARACTERISTICS:
   (A) LENGTH: 24 amino acids
   (B) TYPE: amino acid
   (C) STRANDEDNESS: single
   (D) TOPOLOGY: linear (ii) MOLECULE TYPE: protein (ix) FEATURE:
   (A) NAME/KEY: Protein
   (B) LOCATION: 1..24
   (D) OTHER INFORMATION: /label=NAP-2
      / note= "OPPENHEIM ET AL. (1991) ANN. REV. IMMUNOL.
      9:617-648"

(xi) SEQUENCE DESCRIPTION: SEQ ID NO:3:

Cys Leu Asp Pro Asp Ala Pro Arg Ile Lys Lys Ile Val Gln Lys Lys
1               5                   10                  15

Leu Ala Gly Asp Glu Ser Ala Asp
                20

(2) INFORMATION FOR SEQ ID NO:4:

(i) SEQUENCE CHARACTERISTICS:
   (A) LENGTH: 24 amino acids
   (B) TYPE: amino acid
   (C) STRANDEDNESS: single
   (D) TOPOLOGY: linear (ii) MOLECULE TYPE: protein (ix) FEATURE:
   (A) NAME/KEY: Protein
   (B) LOCATION: 1..24
   (D) OTHER INFORMATION: /label=GRO-A
      / note= "OPPENHEIM ET AL. (1991) ANN. REV. IMMUNOL.
      9:617-648"

(xi) SEQUENCE DESCRIPTION: SEQ ID NO:4:

Cys Leu Asn Pro Ala Ser Pro Ile Val Lys Lys Ile Ile Glu Lys Met
1               5                   10                  15

Leu Asn Ser Asp Lys Ser Asn Tyr
                20